United States Patent [19]
Draganich et al.

[11] Patent Number: 5,658,342
[45] Date of Patent: *Aug. 19, 1997

[54] STABILIZED PROSTHETIC KNEE

[75] Inventors: Louis F. Draganich; Lawrence A. Pottenger, both of Chicago, Ill.

[73] Assignee: Arch Development, Chicago, Ill.

[*] Notice: The term of this patent shall not extend beyond the expiration date of Pat. No. 5,387,240.

[21] Appl. No.: 383,871

[22] Filed: Feb. 6, 1995

Related U.S. Application Data

[63] Continuation-in-part of Ser. No. 976,803, Nov. 16, 1992, Pat. No. 5,387,240.

[51] Int. Cl.[6] ............................................. A61F 2/38
[52] U.S. Cl. ............................................. 623/20
[58] Field of Search .................... 623/16, 18, 20; 606/86, 87, 88

[56] References Cited

U.S. PATENT DOCUMENTS

| | | |
|---|---|---|
| 3,728,742 | 4/1973 | Averill et al. . |
| 3,774,244 | 11/1973 | Walker . |
| 3,996,624 | 12/1976 | Nolles . |
| 4,081,866 | 4/1978 | Upshaw et al. . |
| 4,136,405 | 1/1979 | Pastrick et al. . |
| 4,207,627 | 6/1980 | Cloutier . |
| 4,209,861 | 7/1980 | Walker et al. . |
| 4,213,209 | 7/1980 | Insall et al. . |
| 4,298,992 | 11/1981 | Burstein et al. . |
| 4,892,547 | 1/1990 | Brown . |
| 4,959,071 | 9/1990 | Brown et al. . |
| 5,358,527 | 10/1994 | Forte . |
| 5,387,240 | 2/1995 | Pottenger et al. ............ 623/20 |

Primary Examiner—Debra S. Brittingham
Attorney, Agent, or Firm—Harness, Dickey & Pierce, P.L.C.

[57] ABSTRACT

A semiconstrained prosthetic knee for surgical replacement of a dysfunctional knee includes a tibial platform, a movable bearing element, and a femoral component. The femoral component includes a polycentric convex bearing which slidably engages a movable bearing. The superior surface of the bearing element is designed to congruently slidably engage the inferior surface of the bearing portion of the femoral component throughout the flexion/extension range of the knee. The superior surface of the tibial platform is generally flat and includes at least one protrusion for controlling the movement of the bearing element. A stabilized prosthetic knee also includes a posterior stabilization member and may further include an anterior stabilization member upon the bearing element. The femoral component and the bearing element articulate in at least two radii of curvature and are also provided with an additional articulation surface and a complementary bearing surface. A stabilized prosthetic knee also includes a posterior stabilization member and may further include an anterior stabilization member upon the bearing element. The femoral component and the bearing element articulate in at least two radii of curvature and are also provided with an additional articulation surface and a complementary bearing surface.

25 Claims, 10 Drawing Sheets

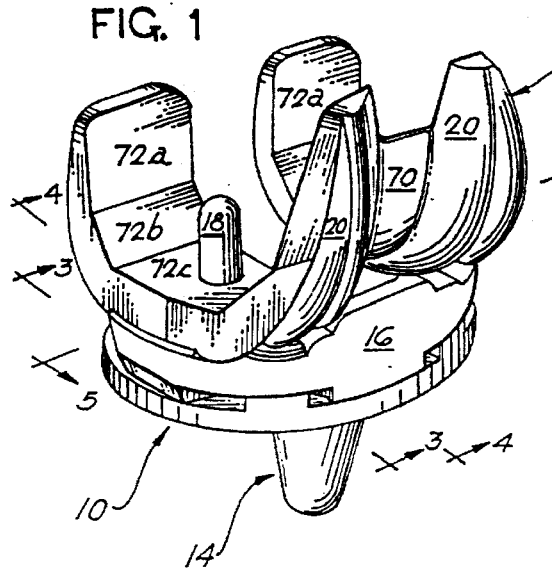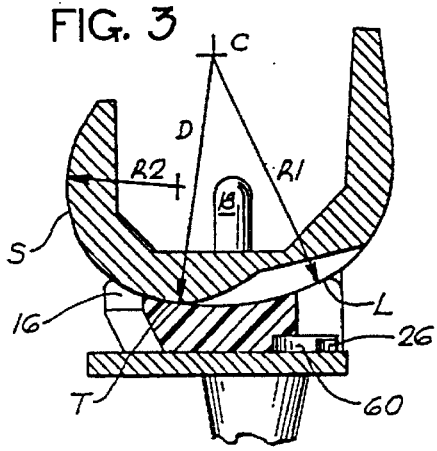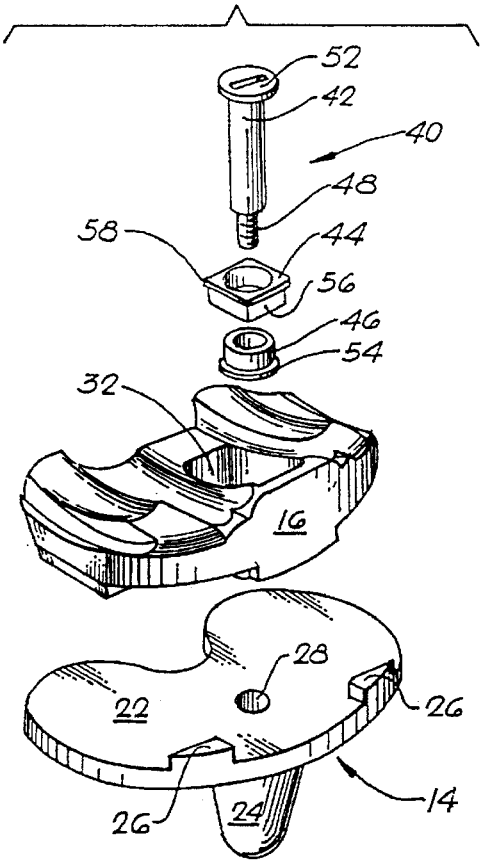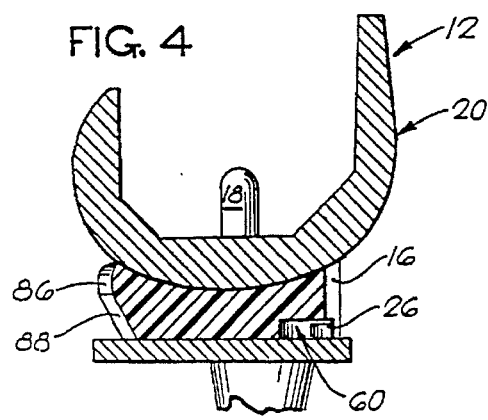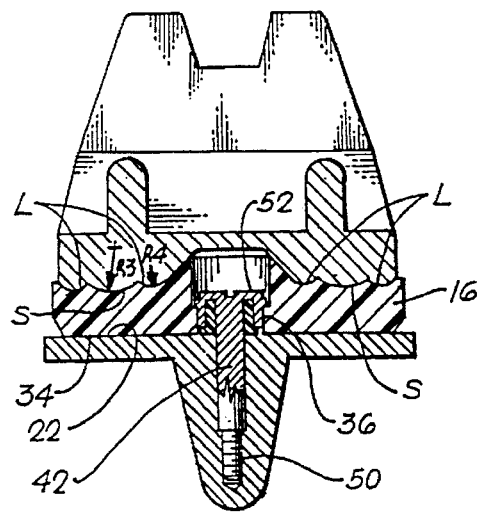

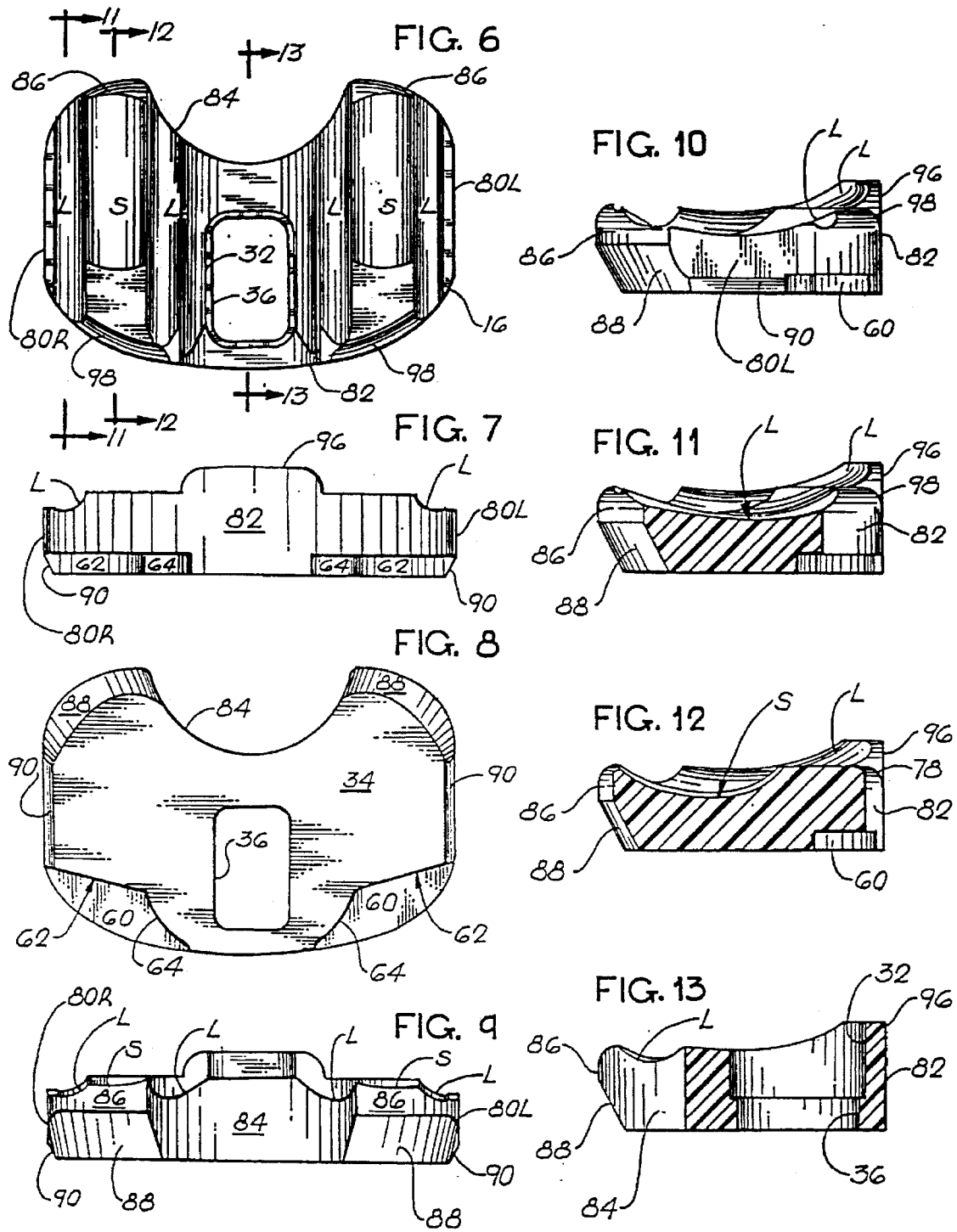

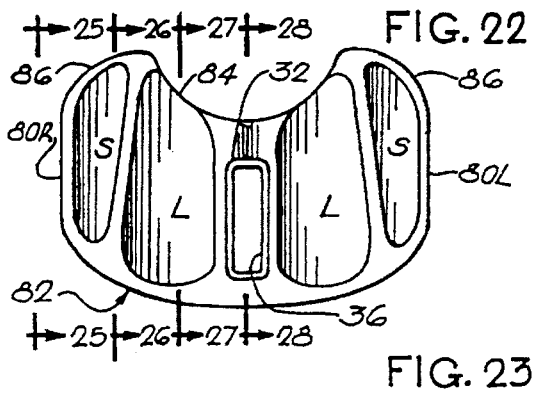
FIG. 22
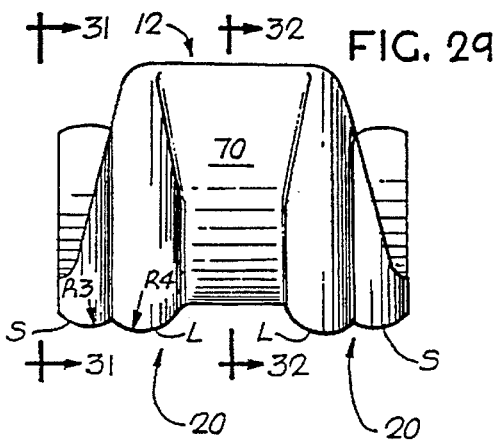
FIG. 29
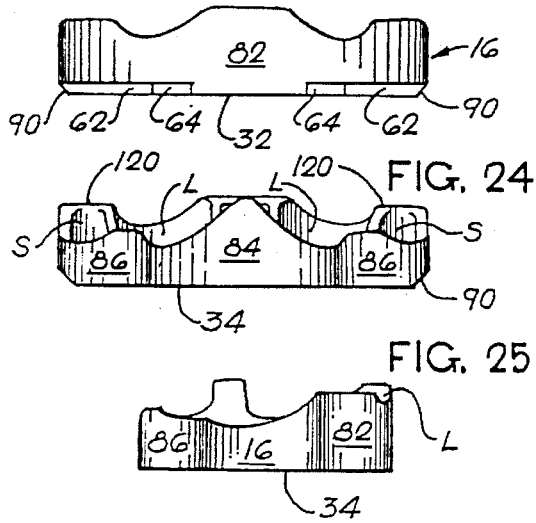
FIG. 23
FIG. 24
FIG. 25
FIG. 26
FIG. 27
FIG. 28
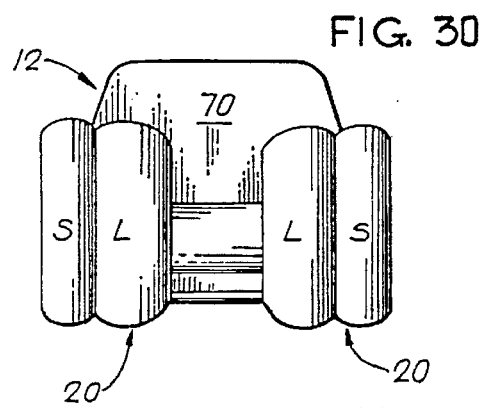
FIG. 30
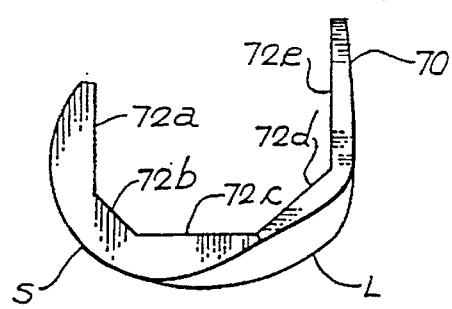
FIG. 31
FIG. 32

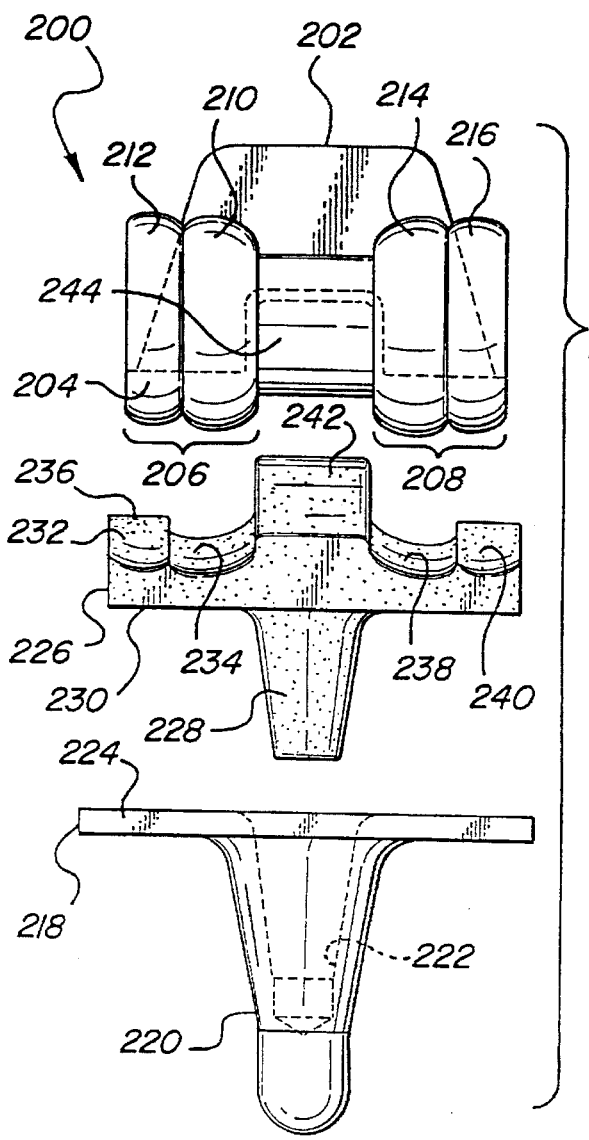
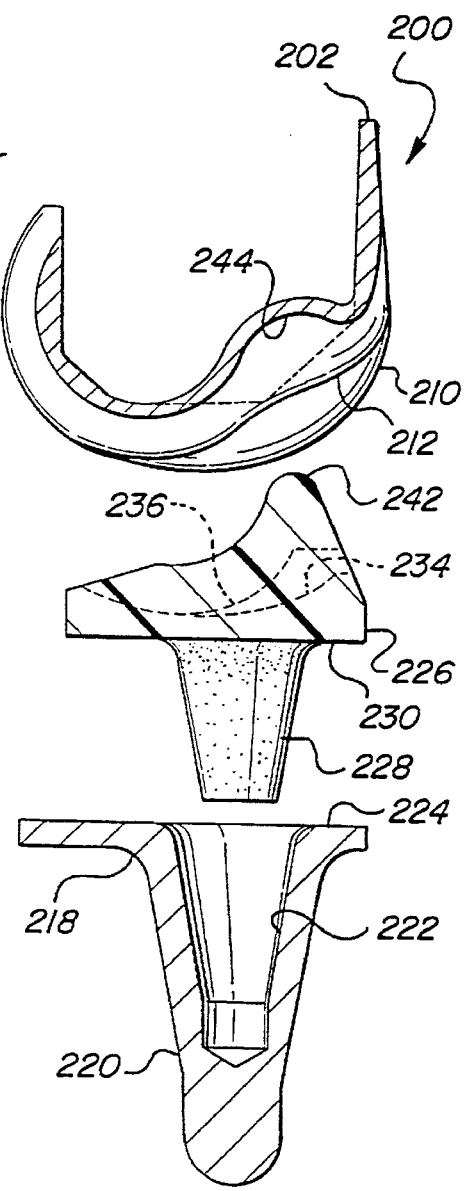
FIG-33
FIG-34

STABILIZED PROSTHETIC KNEE

RELATED APPLICATIONS

This application is a continuation-in-part of U.S. Ser. No. 07/976,803, entitled Improved Floating Bearing Prosthetic Knee, filed Nov. 16, 1992 now U.S. Pat. No. 5,387,240.

BACKGROUND OF THE INVENTION

1. Field of the Invention

This invention relates to prosthetic joints generally, and more particularly to an improved, unconstrained prosthetic knee replacement for a dysfunctional knee.

2. Prior Art

Referring now to prior art knee endoprostheses, there are basically two types of prosthetic replacement knees known generally as constrained and unconstrained knees. An example of an unconstrained or floating meniscal bearing knee is disclosed in Buechel et al U.S. Pat. No. 4,340,978. An embodiment of the Buechel invention is manufactured and sold by Depuy, Inc. of Warsaw, Ind. Preferably, the bearing elements of these types of knees are manufactured with high density polyethylene such as that disclosed in Zachariades U.S. Pat. No. 4,587,163 developed by Polteco Inc. of Alameda, Calif. because of its superior wear resistant characteristics.

Referring next to typical prior art tibial-femoral knee prostheses, prostheses which allow axial rotation and A-P motion in addition to flexion-extension motion have incongruent contact (usually theoretical point-contact) between the femoral and tibial bearing surfaces, have been known. Those prior art knee prostheses which do provide congruent or area bearing contact fail to provide the needed axial rotation, or when cruciates are present the needed anterior-posterior motion.

Preexisting constrained knees have often resulted in early failure as a result of hinge constrainment. The degree of rotation was limited to either only one plane or a very small arc. Also, as shown in U.S. Pat. No. 4,219,893, very little flexibility was possible in the shape of the patello-femoral interfaces because of the requirement to maintain congruent patello-femoral contact over the range of motion of the knee. As a result, patello-femoral tracking problems became commonplace.

It was necessary to use a large circumference when used to resurface allografts resulting in problems with soft tissue necrosis and/or patello-femoral tracking problems as described above. Furthermore, most implants were known as custom devices since they had to be specially made to fit a particular patient's size and thus required excess manufacturing time and unnecessary delays.

An additional, significant problem with prior art constrained knees results from the fact that the range of motion prevents the normal A-P movement of the inferior end of the femur relative to the posterior end of the tibia. This "sliding" movement is necessary in order to maintain the full range of motion desired in a prosthetic device.

Current prostheses of the dislocatable cruciate retaining type, such as the Geomedic knee replacement shown in U.S. Pat. No. 3,728,742 to Averill et al, that produce area contact provide only one axis of rotation relative to the femur for the flexion-extension motion. Normal flexion-extension is, however, characterized by a polycentric flexion-extension motion where rotation relative to the femur occurs about many axes.

This polycentric motion, which results from the action of the cruciate ligaments and condylar shape, allows for more efficient utilization of muscle forces by providing a posterior shift of the axis when effective quadriceps action is important and an anterior shift when hamstrings effectiveness is important. Furthermore, in the human knee it is this action and the A-P shift, and the shape of the posterior condyles, which influence this motion so as to allow full flexion capability for the knee. Failure to provide appropriate knee geometry inhibits, when cruciate ligaments are present, this natural motion and thus tends to restrict muscle effectiveness and inhibit flexion. These restrictions tend to increase both loading on the prosthesis and loading between prosthesis and bone.

Another problem exists with regard to knee endoprostheses for implantation in those cases wherein the cruciate ligaments are functionally absent but where the collateral ligaments are functional or at least reconstructible. In the absence of cruciate ligaments, the prosthetic replacement must provide anterior-posterior knee joint stability so as to replace that stability otherwise provided by the cruciates. Until recently most such cases were treated by a constrained type knee prosthesis.

Where the cruciate ligaments are present, most surgeons would prefer their retention, since they provide important internal stabilizers and, together with the condylar geometry of the femur and tibia, control the rotation axis and A-P motion of the knee. Furthermore, these ligaments provide anterior-posterior stability. Thus, it is desirable to reserve the cruciate ligaments, even though reasonable stability can be provided by a properly designed full platform type prosthesis.

In addition, the action of the cruciate ligaments produces a shift in the rotation axis of the knee which results in more efficient muscle utilization. Thus, preservation of these structures provides better physiological function after knee replacement.

It is not, however, clear that the physiological advantages gained in retaining the cruciates outweigh the disadvantages of the design compromises, such as increased bearing surface incongruency and reduced tibial prosthesis bearing area, required to retain these ligaments. Thus, the desirability of retaining the cruciate ligaments in the cases of unconstrained knee replacement is not well established.

A recent unconstrained knee concept, the New Jersey knee, appears to provide a partial solution to the problem of overconstraint while attempting to maintain congruency by the use of meniscal floating elements. Unfortunately, this knee suffers from several design problems which appear to limit its usefulness.

The present invention, the Pottenger/Draganich Knee utilizes new concepts combined in an improved design in order to avoid some of the anticipated difficulties of the prior art design.

SUMMARY OF THE INVENTION

The present invention is directed to an improved prosthesis for the replacement of all or a portion of a dysfunctional human knee joint.

An object of the present invention is to provide an improved semiconstrained knee prosthesis with a novel polycentric femoral component having different radii of curvature in different sagittal sections.

An object of the present invention is to provide a knee prosthesis which facilitates rotation about one or more axes in the presence of congruency of the bearing surfaces.

A further object of the present invention is to provide a knee prosthesis which substantially reduces the possibility of tipping and/or dislocation of the bearing insert or inserts in the absence of the anterior and posterior cruciate ligaments.

A further object of the present invention is to provide a knee prosthesis which allows full flexion of the reconstructed knee without applying shear forces.

A further object of the present invention is to provide a knee prosthesis where the tibiofemoral area contact controls the movement of the femoral component and thus increases quadriceps effectiveness.

An object of the present invention is to provide a knee prosthesis in which A-P sliding of the bearing element with knee flexion allows the normal anatomical shift in the center of the area of contact between femoral and tibial condyles.

A further object of the present invention is to provide a knee prosthesis with improved medial-lateral stability, substantially unaffected by axial rotation or anterior-posterior (A-P) shift of the bearing element.

A further object of the present invention is to provide a knee prosthesis which includes constraints at the limits of normal motion to compensate for missing cruciate ligaments and prevent dislocation.

A further object of the present invention is to provide a semiconstrained knee prosthesis where the femoral component may articulate in extremely close proximity with the tibia to eliminate patella baha problems.

In accordance with the foregoing and other objects, the unconstrained prosthetic knee of the present invention includes a femoral prosthesis having a pair of condylar portions, each having, preferably two sagitally spaced arcuate segments of different radii, a tibial prosthesis having a bearing surface for supporting weight, and an intermediate load-bearing member having a thrust-bearing surface for matingly engaging the bearing surface of the tibial prosthesis and adapted to distribute weight and to transmit forces in a plane substantially perpendicular to the axis of the tibia and a mutually congruent superior surface for engaging the condyles of the femoral prosthesis to provide area contact throughout the full range of flexion/extension of the knee.

A further object of the present invention is to provide a knee prosthesis that is stabilized in its anterior and/or posterior movement throughout a substantial range of flexion.

In accordance with the foregoing and other objects, the stabilized prosthetic knee of the present invention includes a posterior stabilization member and may further include an anterior stabilization member upon an intermediate bearing member. A femoral component articulates in at least two radii of curvature with the bearing member. The bearing element rotates with respect to a tibial component, and the posterior and anterior stabilization members inhibit disarticulation between the bearing element and a first bearing surface of the femoral component.

BRIEF DESCRIPTION OF THE DRAWINGS

A complete understanding of the invention may be obtained from the detailed description which follows, together with the accompanying drawings, wherein:

FIG. 1 is a perspective view of one embodiment of the unconstrained prosthetic knee of the present invention;

FIG. 2 is an exploded perspective view of the tibial component and bearing element of the prosthetic knee of FIG. 1;

FIG. 3 is a vertical section taken generally along the line 3—3 of FIG. 1;

FIG. 4 is a vertical section taken generally along the line 4—4 of FIG. 1;

FIG. 5 is a vertical section taken generally along the line 5—5 of FIG. 1;

FIG. 6 is a top plan view of the bearing element made in accordance with the present invention as shown in FIG. 1;

FIG. 7 is a front elevational view of the bearing element of FIG. 6;

FIG. 8 is a bottom view of the bearing element of FIG. 6;

FIG. 9 is a rear elevational view of the bearing element of FIG. 6;

FIG. 10 is a side elevational view of the bearing element of FIG. 6;

FIG. 11 is a vertical section taken generally along the line 11—11 of FIG. 6;

FIG. 12 is a vertical section taken generally along the line 12—12 of FIG. 6;

FIG. 13 is another vertical section taken generally along the line 13—13 of FIG. 6;

FIG. 22 is a top plan view of the bearing element made in accordance with the preferred embodiment of the present invention;

FIG. 23 is a front elevational view of the bearing element of FIG. 22;

FIG. 24 is a rear elevational view of the bearing element of FIG. 22;

FIG. 25 is a side elevational view taken along the line 25—25 of FIG. 22;

FIG. 26 is a vertical section taken generally along the line 26—26 of FIG. 22;

FIG. 27 is a vertical section taken generally along the line 27—27 of FIG. 22;

FIG. 28 is a mid-vertical section taken generally along the line 28—28 of FIG. 22;

FIG. 29 is a front elevational view of the femoral component of the preferred embodiment.

FIG. 30 is a bottom plan view of the femoral component of the preferred embodiment;

FIG. 31 is a side elevational view of the femoral component taken generally along the line 31—31 of FIG. 29;

FIG. 32 is a mid-vertical section of the femoral component taken generally along the line 32—32 of FIG. 29.

FIG. 33 is an exploded rear elevational view of the knee of the present invention including a posterior stabilization member;

FIG. 34 is an exploded side cross-sectional view of the embodiment of the knee shown in FIG. 33;

BRIEF DESCRIPTION OF THE PREFERRED EMBODIMENT

Figure 14:
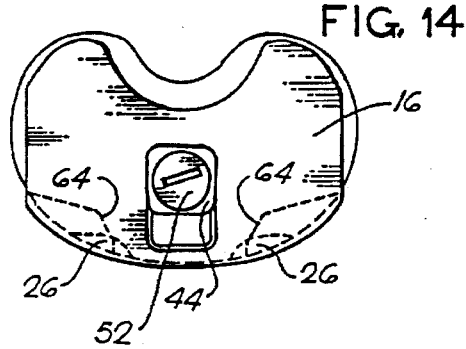
FIG. 14 is a diagrammatic representation of the assembled bearing element and tibia portion showing the bearing element in its forwardmost position.

The prosthetic knee of the present invention is shown and described herein with respect to two embodiments. The two embodiments differ in the number of arcuate surfaces provided for sliding engagement between the femoral component and the bearing element as described in detail hereinafter. The embodiment shown and described in FIGS. 1–21 describe the prosthetic knee design utilizing three arcuate surfaces on each of the condyles of the tibial component. The preferred embodiment, shown in FIGS. 22–32 utilizes only two arcuate surfaces for the improved knee as shown and described in detail herein. For convenience, the same numerals are used to describe the same element in the respective embodiments.

The floating bearing prosthetic knee, generally designated 10 in FIG. 1, provides area contact as opposed to line contact or point contact throughout the entire flexion/extension range of the prosthesis. Through this design, some degree of rollback automatically occurs as the knee flexes and additional rollback is allowed to will occur through the movement of the sliding bearing. Area contact throughout the full range of motion is obtained through the use of multiple arcuate sections along the path of conduct of the condyles with the bearing insert. However, unlike prior art prosthetic knees of the prior art, the different radii and arcuate portions of the condyles lie in different sagittal or medial-lateral planes. Thus tibial-femoral area contact will occur in different longitudinal planes throughout the flexion/extension range of the knee. Area contact will occur simultaneously in two planes only at the point of transition between the respective arcuate portions.

The desirable prosthetic knee 19 satisfies at least five characteristics. One, the knee should have the normal polycentric motion of the normal knee joint. Two, unconstrained anterior-posterior motion and rotation would be permitted within the normal range of motion of the knee. Three, constrained A-P motion and rotation would occur at the limits of normal motion. Four, normal rollback of the femur with respect to the tibia should occur during flexion of the knee. Five, tibial-femoral contact pressure should be minimized in order to reduce wear on the polyethylene bearing insert 16. The present invention 10 satisfies these five characteristics as described hereinafter.

MAJOR COMPONENTS

Referring now in particular to FIG. 1, the unconstrained knee, generally designated 10, is shown in perspective view to include a femoral component 12, a tibial component 14, and a bearing element 16. The femoral component 12 includes at least one upwardly extending stem 18 or other means for connection to the femur and a pair of condyles 20 on its inferior surface for engagement with the bearing portion 16. Preferably, the bearing element 16 is constructed of a tough, wear-resistant, resilient material such as high density polyethylene. The remaining elements of the prosthetic knee are metallic and preferably manufactured of a cobalt-chromium alloy material approved for use in prosthetic devices.

THE TIBIAL COMPONENT

The tibial component includes a generally flat rigid platform 22 and a depending stem portion 24 for securing the tibial portion to the tibia. The superior surface of the femoral component and the implantable stem portion 24 and inferior surface of the platform 22 of the tibial component include a surface adapted for porous ingrowth to secure the prosthetic device within the tibia and femur, respectively, of the host or allograph bone of the patient. By contrast, the condyles 20 of the femoral component are highly polished to reduce friction.

Referring to the lower portion of FIG. 2, the tibial portion includes the platform 22 and the depending stem 24. The platform is provided with a pair of laterally spaced, generally triangular-shaped, upward protrusions 26 and a centrally located aperture 28 for limiting the A-P movement of the bearing 16 described below.

More particularly, referring to FIGS. 2, 5 and 6, the bearing 16 includes a centrally located generally rectangular opening 32 which is used to slidably connect the bearing to the top of the tibial component 22. The bearing 16 has a generally flat inferior surface 34 as shown in FIG. 8 which slidably engages the superior surface or platform 22. The aperture 32 includes, at its lower end, a ridge or lip 36, of similar configuration. Both the aperture 32 and the vertical wall of the bearing have smooth or rounded corners to reduce stress. The bearing 16 is captured by a retaining means, generally designated 40, which includes a shoulder bolt 42, a retainer 44 and a spacer 46. The spacer 46 and retainer 44 are preferably manufactured of high density polypropylene, similar to that used for the bearing insert 16 and the shoulder bolt 42 would be made of stainless steel, titanium or cobalt-chromium alloy approved for use in this application.

The shoulder bolt 42 includes a lower threaded portion 48 which engages a plurality of threads 50 at the lowermost end of the aperture 28 within the stem 24 of the tibial component. The shoulder sets the depth to prevent from the head 52 of the shoulder bolt from impeding the movement of the bearing insert 16. The retainer 46 includes an enlarged diameter ring 54 at its lowermost end which engages the platform 22 of the tibial portion 14 around the aperture 28 and extends upwardly coaxially with the shoulder bolt 42.

The retainer or retaining element 44 is generally square in shape and includes a lower square portion 56 which forms a clearance fit within the ridge 36 at the lower end of the aperture 32 in the bearing, as can be seen in FIG. 5. The upper end of the retainer includes an enlarged flange 58 which engages the top of the step or lip 36. The retainer 44 is dimensioned so that the distance between the underside of the head 52 of the shoulder bolt and the top of the lip 36 provides a low tolerance clearance fit with the flange 58 of the retainer to allow the bearing 16 to slidably move on the platform 22 without becoming disengaged from the platform 22. In this manner, the bearing is free to slide in an anterior posterior or A-P path. The retainer 44 will stop the movement in the A-P direction as the front and rear surfaces engage the front or inner surfaces of the lip 36.

The retaining means 40, in addition to permitting A-P movement of the bearing 16 also permits pivotal movement generally about the center line of the shoulder bolt 42. Thus, depending upon the anterior or posterior displacement of the bearing insert 16 relative to the retainer 44, the bearing insert and the retainer may pivot about the center line of the shoulder bolt 42 to provide freedom of movement. However, in order to prevent too much pivotal movement of the bearing 16, particularly when in its anteriormost position, the triangular protrusions 26 provide a stop means.

Figure 15:
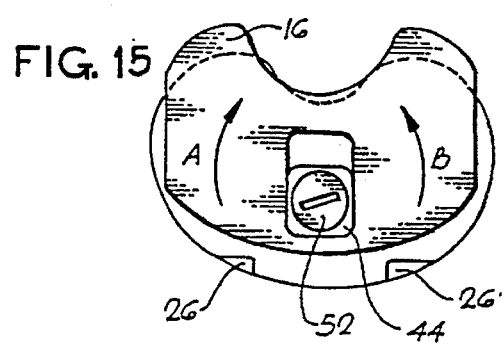
FIG. 15 is a diagrammatic representation similar to FIG. 14 showing the bearing element in its rearwardmost position.

The stop means includes the upward protrusions 26 and a pair of symmetrical cutouts 60 on the lower surface of the bearing insert 16. In particular, each cutout includes a generally flat rear wall 62 and a generally curved inner wall 64 for engagement with the upward protrusions 26. As shown in FIG. 4, the height of the rear wall 62 permits the cutouts 60 to clear the top of the stops 26. Referring to FIG. 14, in its anterior-most position, the arcuate walls 64 of the bearing 16 engage the inner, generally right angle corner of the triangular protrusions 26 to virtually preclude most of the pivotal, movement or rotational movement of the bearing insert 16. As the bearing 16 is moved towards its posterior-most position, as shown in FIG. 15, the bearing is free to rotate in either direction as shown by arrows A and B and are limited by the longer upstanding walls of the protrusions 26 which engage the flat walls 62 within the cutout 60.

Figure 16:
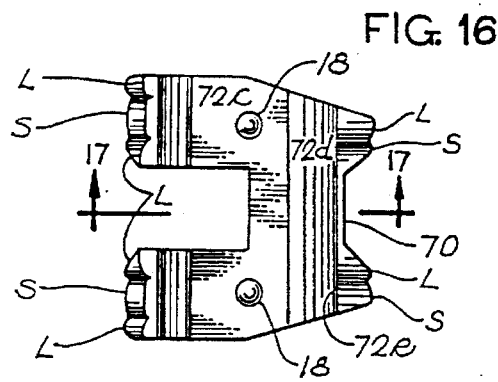
FIG. 16 is a top plan view of the femoral component on a reduced scale.
Figure 17:
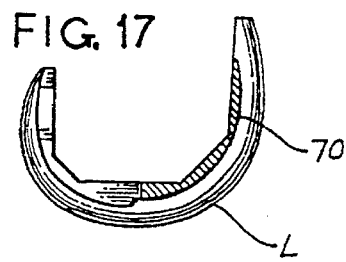
FIG. 17 is a vertical section taken generally along the line 17—17 of FIG. 16.
Figure 18:
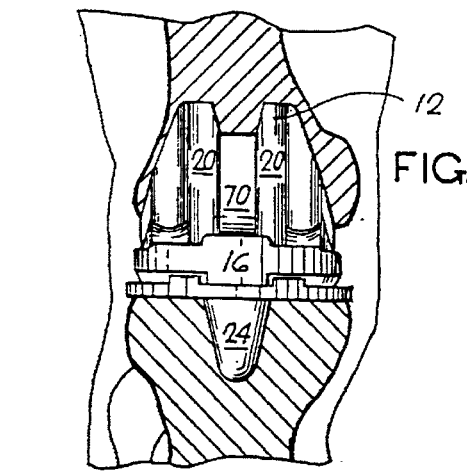
FIG. 18 is a front elevational view of the prosthesis assembly of FIG. 1 implanted within a patient.
Figure 19:
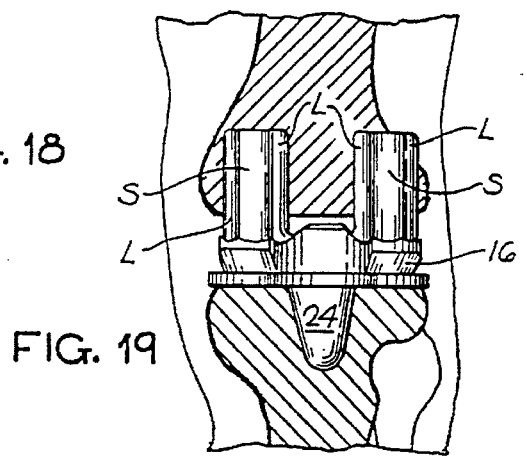
FIG. 19 is a rear elevational view of the prosthesis assembly of FIG. 1 implanted within a patient.

Therefore, it can be seen that the bearing insert 16 is constrained but is permitted to move in the A-P direction from the extremes as shown in FIG. 14 to that as shown in FIG. 16 while, at the same time, it is free to pivot about an axis defined by the shoulder bolt 24 within the limits created by the stop means where the walls 62 and 64 of the cutouts 60 engage the triangular protrusions 26. These constraints, while permitting movement of the bearing 16, control the movement of the femoral component as described hereinafter and thus create some rollback and allow for the further posterior movement of the bearing insert.

These constraints at the limits of normal motion will compensate for missing cruciate ligaments and prevent dislocation of the components, i.e., the bearing insert, which has been seen to occur in popular prior art floating bearing prosthetic knees. In most circumstances, normal soft tissue will provide the primary restraining forces limiting motion of the components and, if necessary, the limits incorporated into the prosthesis 10 would function as secondary restraints.

Some rollback (approximately 5 millimeters in the present embodiment) automatically occurs (i.e., is obligated to occur) when tibiofemoral contact moves from one arcuate segment to the other one. The rest of the normal amount of rollback is allowed to occur (but not obligated to occur) with the movement of the bearing insert. The amount of additional rollback that is allowed to occur is governed by the interaction of the posterior cruciate ligament and the condylar surfaces. The rollback of the femur with respect to the tibia during flexion of the knee is an important characteristic of the present prosthesis because it causes the patellar tendon to move anteriorly with respect to the femur which greatly increases the effectiveness of the quadriceps muscle, especially when rising from a chair. It has been found that many patients who have had total knee replacements cannot get up from a sitting position without assistance from their arms. Also, prior art unconstrained knees are frequently found to "roll forward" rather than backward during flexion. In the design of the present invention, the shoulder bolt retaining means 40 prevents roll forward and the bearing insert 16 recreates the normal situation and further helps to increase the quadriceps efficiency. Known prior art total knee replacements have attempted to utilize the femoral component to control the motion of the bearing insert, just the opposite of the knee of the present invention.

THE FEMORAL COMPONENT

Figure 20:
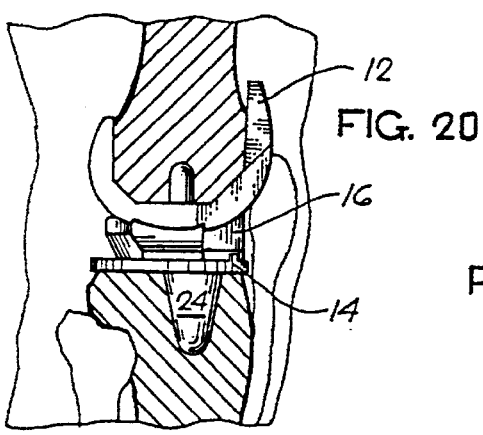
FIG. 20 is a side elevational view of the prosthesis assembly of FIG. 1 in a generally, straight extended position.

The femoral component 12 of the present invention includes generally a pair of condyles 20, securing posts 18 and a web portion which defines a patella track 70. The securing posts 18 provide means to secure the femoral component to the femur of a patient. As shown in FIG. 20, a pair of matched apertures are drilled into the femur and the end of the femur is formed with five generally flat surfaces as shown to fit within the flat surfaces 72a through 72e as shown. The opposite surfaces 72a and 72e are generally parallel to one another and perpendicular to the surface 72c. The angled surfaces 72b and 72d are approximately at 45 degrees with respect thereto. The entire surface of the flat surfaces 72a–e and the surfaces of the posts 18 are designed for extramedullary bone growth to secure the femoral component to the end of the femur.

Certain prior art prostheses propose the use of a femoral component in which the multicentric surfaces of the condyles were created by a common planar curve which created a design whereby every sagittal section along the condyle was polycentric. This design results in a situation where the condyles can only make area contact during approximately the initial 20° of knee flexion thereby resulting in line contact and very high contact pressure which increases the wear of the bearing insert. In addition, prior art design of this type accommodates rollback of the femur with respect to the tibia and, particularly at maximum flexion, there is a tendency for the bearing insert to "pop out" or become dislocated.

The femoral component and sliding bearing of the present invention have congruent surfaces which allow for rotation and A-P motion within the range of normal A-P motion to prevent excessive anterior and posterior drawer and rotation and dislocation of the bearing. The upper surface of the bearing 16 is designed so that the inferior surfaces of the femoral component always have area contact at all flexion angles. Constant area contact is achieved by distributing the femoral contact areas on the bearing 16 across the frontal plane such that different areas of the bearing 16 are contacted through different angles of knee flexion. Each contact area on the bearing has the same radius of curvature as the portion of the inferior surface of the femoral component 12 in contact with the bearing.

THE BEARING INSERT

Referring to FIGS. 6–13, the bearing insert 16 is generally oval in shape with a pair of flat ends 80R and 80L. The anterior or front side is a generally flat arcuate wall 82 which includes a pair of cutouts 60 at the lower right and left ends, respectively. The posterior side includes a relatively large, almost semicircular recess 84 which provides substantial clearance for the posterior cruciate ligaments. The top portion of the rear wall on either side of the recess 84 includes a short generally vertical arcuate wall portion 86 which merges into a generally arcuate, inwardly tapered lower wall portion 88. The tapered portions 88 merge with a pair of lower chamfers at the bottom of the end walls 80R and 80L which terminate at their front ends with the cutouts 60.

The superior surface of the bearing insert is described by a plurality of arcuate channels or grooves which are described in detail hereinafter in connection with the arcuate surfaces defined on the inferior contact surface of the femoral component. In order to add rigidity to the front wall portion 82, an upstanding flange 96 is included immediately anteriorly of the aperture 32. The outer edges of the top of the front wall 82 are softened by curves 98 as the transition to the top of the bearing insert 16.

CONTACT SURFACES

The contact surfaces between the bearing insert 16 and the femoral component 12 are best understood if considered together. The upper surface of the bearing 16 includes a plurality of arcuate surfaces for engagement with congruent arcuate surfaces on the inferior side of the femoral component 12. Referring to FIG. 6, four of the arcuate surfaces have been labelled L and two of the surfaces have been labelled S. The four arcuate surfaces L are all generated using the same radius of curvature and similarly the two arcuate surfaces labelled S are generated using the same radius, which is smaller than the radius used to generate the surfaces L. The arcuate surface S shown in section view in FIG. 12 is defined posteriorly of the arcuate surfaces L, one of which is shown in sectional view in FIG. 11. As can be seen in FIG. 5, the complementary surface of the femoral component includes four arcuate surfaces L and two arcuate surfaces S. One significant feature of the present invention is that the arcuate surfaces L and R lie in different sagittal planes as shown and make contact during different degrees of flexion of the knee.

In particular, the arcuate surfaces L on the inferior surface of the femoral component are in contact with the arcuate surfaces L on the bearing 16 between approximately 0° through 8° of flexion of the knee and the arcuate surfaces S of the femoral component are in contact with the arcuate surfaces S of the bearing 16 during approximately 8° through 140° of flexion of the knee. At the transition point, at approximately 8° of flexion, area contact occurs between all of the arcuate surfaces L and S on the femoral component 12 with all of the arcuate surfaces L and S on the bearing component 16.

Although the size of the patient will partially determine the size of the prosthesis, the following sizes have been found to be effective in trials. More particularly, referring to FIG. 3, the arcuate surfaces L are generated by radius R1 about a center point C. Center point C is slightly rearwardly defined relative to the post 18 and the radius R1 is approximately 1.60". The arcuate surfaces S are generated by a radius R2 about a center of rotation D. The radius R2 is approximately 0.75". The center of rotation D of radius R2 lies on a line passing through the center of rotation C of R1 so that the surfaces L and R have a tangent point T in order to have a smooth transition of tibia-femoral contact at approximately 8° of flexion. Thus, area contact of the arcuate surfaces L occurs during the first 8° of flexion of the knee and area contact is transferred to the arcuate sections S at approximately 8° and continues through maximum flexion of about 140°.

The position of the femoral component 12 with regard to the bearing 16 is controlled by the center of rotation of curvature for the arcuate surfaces S or L which are in contact. The arcuate curves S are placed farther back on the bearing and will draw the femoral component posteriorly thus allowing obligatory rollback. Further rollback is permitted because the elongated aperture 32 in the bearing allows the bearing to move posteriorly on the tibial platform. As described previously, the constraints 26 and the retaining means 40 prevent anterior movement of the bearing 16 beyond the anterior edge of the tibial component. Therefore, when rollback is occurring during flexion of the knee, no compensatory roll forward will occur between the bearing 16 and the tibial component 14. As the femoral component passes through approximately the 8° range, area contact is transferred between the arcuate surfaces L to the arcuate surfaces S, the transition continues smoothly because of the common tangent point of the respective arcuate surfaces. The constraints as previously described with respect to the bearing 16 prevent dislocation of the bearing element when implanted.

In an alternative embodiment, it is possible to obtain the same functionality and operation if, for example, the innermost or outermost complementary arcuate surfaces L were eliminated. However, additional area contact can be obtained to decrease the pressure between the femoral component and the bearing by providing the additional arcuate surfaces L adjacent the center aperture 32.

In addition, the arcuate surfaces L and S are designed to obtain the maximum amount of area contact possible within the permissible space. To this end, the arcuate surfaces S on the bearing 16 are approximately ⅜" wide and approximately 1⅛" long. As described previously, the radius R2, the radius for generating the arcuate surface S is approximately 0.75" and lies in a sagittal plane. The transverse radius which defines the arcuate surface in the medial lateral plane as shown in FIG. 5 is approximately 0.375". Similarly, the arcuate surfaces L are approximately 1.25" in length generated by the radius R1 in the sagittal plane and the radius in the transverse plane R4 (FIG. 5) which defines a radius of curvature of the arcuate surfaces L in the transverse plane is approximately 0.125". The center of rotation D is approximately 0.375" posteriorly of the center of rotation C and about 0.9" below the center of rotation C. The centerlines of the arcuate surfaces L are approximately 0.3" on either side of the centerline of the arcuate section S and the respective centerlines of the arcuate sections S are approximately 2.00" apart.

FIGS. 22–32 describe the preferred embodiment of the present invention, which as described previously, is simpler in design and provides better performance. The preferred embodiment differs in several respects but primarily in the number of arcuate surfaces in contact between the femoral component 12 and the bearing surface 16. In particular, this embodiment uses two arcuate surfaces on either side of the midline of the femoral component and the bearing surface as to the design which includes three arcuate surfaces described previously with respect to the embodiment shown in FIGS. 1–21.

Referring to FIG. 29, the femoral component includes a pair of condyles 20 each of which includes two arcuate surfaces L and S. In particular, the arcuate surfaces L on the inferior surface of the femoral component are in contact with congruent arcuate surfaces L on the bearing element 16 between approximately 0° and 8° of flexion of the knee. The arcuate surfaces F of the femoral component are in contact with the arcuate surfaces S of the bearing element 16 during approximately 8° through 140° of flexion of the knee. At the transition point, at approximately 8° of flexion, area contact occurs between all of the arcuate surfaces L and S of the femoral component 12 with all of the arcuate surfaces L and S on the bearing component 16. At this transition point in flexion, contact shifts between surfaces L to surfaces S in a smooth, natural manner because again, as shown in FIG. 3, the arcuate surfaces S and L are tangent to one another at this instant during flexion of the knee. As described previously, this common tangent point is a significant advantage and is a feature that is not shown in any prior art devices. FIG. 3 shows in detail the two radii R1 which generates the arcuate surface L and R2 which generates the arcuate surface S have a common center of rotation where the center of rotation of R2 lies on the radii R1 at point D so that a line tangent to R1 and R2 can be drawn only at the point where a line through points C and D intersect the arcuate surface.

It had been suggested in a prior European Patent No. 0,346,183 to Henri Judet, published Dec. 13, 1989, that multiple radii may be advantageous. However, there was no disclosure like the knee herein showing a clear misunderstanding of the requirements for natural knee movement. Judet had no common tangent point at any contact portion between the femoral component and the bearing surface to permit a smooth transition from one surface to the other. The present inventors recognize this important advantage which had never previously been recognized.

The position of the femoral component 12 of FIG. 29 with regard to the bearing element 16 of FIG. 22 is controlled by the center of rotation of curvature for the arcuate surfaces S or L which are in contact. The arcuate surfaces S are placed further back on the bearing and will draw the femoral component posteriorly, thus allowing obligatory rollback. Further rollback is permitted because the elongated aperture 32 in the bearing allows the bearing to move posteriorly on the tibial platform. As described previously, the constraints 26 on the tibial platform and the retaining means 40 prevent anterior movement beyond the interior edge of the tibial platform. Preferably, the lower surface of the bearing element shown in FIG. 22 includes the cutouts 60 defined by the walls 62 and 64 to receive the constraints 26 near the anterior surface of the tibial platform. Therefore, when rollback is occurring during flexion of the knee, no compensatory roll forward will occur between the bearing 16 and the tibial component 14 as the femoral component passes through approximately the 8° range, area contact is transferred between the arcuate-surfaces L to the arcuate surfaces S and the transition occurs smoothly because of the common tangent point of the respective arcuate surfaces. The constraints as previously described with respect to the bearing 16 prevent dislocation of the bearing element when implanted.

In the preferred embodiment, as shown in FIGS. 24 and 25, the arcuate surfaces S terminate in a high front wall 120 which provides for a substantially longer, forwardly extended arcuate surface S which provides substantially enhanced posterior stability. This feature will permit the retention of the cruciate ligament if desired.

The use of two instead of three arcuate surfaces on each condyle portion 20 permits the use of a larger radius in the M-L direction. In contrasting FIG. 5 of the first embodiment with FIG. 29 of the preferred embodiment, it can be seen that the radius R3 which defines the arcuate surface S and the radius R4 which defines the arcuate surface L are larger, therefore providing substantially more contact area for a particular prosthesis. Again, the size of the prosthetic knee of the embodiment shown in FIGS. 22–30 will again vary for each patient. However, the general or approximate dimensions described with respect to the embodiment shown in FIGS. 1–20 will be similar with respect to the embodiment of FIGS. 22–32 except that the radii defining the arcuate surfaces in the transverse plane are substantially larger. The larger radius R3 is particularly advantageous when encountering liftoff as described previously. The larger surface area of the larger arcs provide substantial additional stability.

The knee prosthesis 10 of both embodiments of present invention is the only design which gives area contact between the bearing 16 and the femoral component 12 in all degrees of flexion. The highest pressures on the knee joint are experienced during stair climbing where the knee is flexed to approximately 90 degrees of flexion in which the prior art knees have only line contact or point contact. Since polyethylene (the material used to form the bearing) wear appears to be related to excessive pressures, area contact is more important in stair climbing or rising from a chair than when walking, even though the former may be performed much less often. The prosthetic knee 10 also permits the use of the same component in the presence or absence of posterior cruciate ligaments. Generally speaking, semiconstrained knee prosthesis require the presence of posterior cruciate ligaments to prevent posterior subluxation of the tibia. On the other hand, constrained prosthesis, which do not allow rollback, require removal of the posterior cruciate ligaments because proper tension on the posterior cruciate ligaments would attempt to create posterior rollback which is prevented by the constraints. This could lead to dislocation of the components of the constrained prosthesis or rupture of the posterior cruciate ligaments.

In prior art designs in which the arcuate surfaces of the condyles are created by using a common plane generating curve, all of the sagittal sections of the condyles are polycentric. On the contrary, the present invention has only one radius of contact in each sagittal plane and, therefore, is not created by a common plane generating curve. Since all potential points of contact in the sagittal plane have the same radius of curvature, area contact can be obtained throughout the entire flexion arc of the knee in a manner which cannot be obtained by the prior art knees where the radii along the condyles changes while contacting the same area of the bearing insert.

Figure 21:
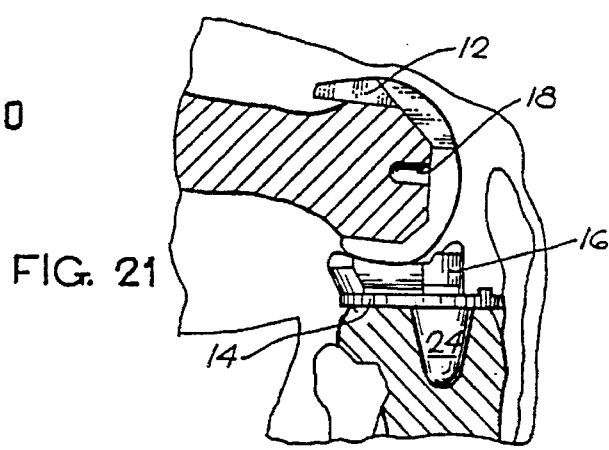
FIG. 21 is a diagrammatic representation of the prosthesis assembly of FIG. 1 with the knee shown in flexion.

Referring to FIGS. 18–21, which show the movement of the elements of both embodiments of the prosthetic knee 10 of the present invention implanted in a patient, it can be seen in FIG. 20 that in the extended position of the prosthesis, the bearing insert 16 moves to its anterior-most position with respect to the tibial component 14. In this position, the arcuate surfaces L on the respective tibial component and bearing insert 16 are in engagement. As the knee flexes, rollback of the femur with respect to the tibia begins to occur to approximately the maximum position as shown in FIG. 21 where the bearing insert 16 has moved to its posterior-most position emulating, as close as possible, the normal knee.

Thus, it can be seen that the present invention defines and describes a prosthetic knee which more closely simulates the normal knee movement than any prior art devices. The prosthesis 10 provides normal polycentric motion for the knee joint and permits normal rollback of the femur with respect to the tibia during flexion. The rotational and anterior-posterior movement of the bearing insert is unconstrained for the normal range of motion but is constrained at its limits. The design of the polycentric-contact surfaces between the femoral component 12 and the bearing insert 16 assure for sufficient area contact throughout the flexion/extension range of the knee to minimize pressure and resultant wear on the bearing insert.

While it has been found that the design of the prosthetic knee 10 of the present invention as shown and described with respect to FIGS. 22–32 are preferable, the inventors recognize that additional improvements could be made utilizing the common tangent point contact transition feature of the present invention and, therefore, while the foregoing detailed description has been given for clearness and understanding, no unnecessary limitations should be understood therefrom as some modifications will be obvious to those skilled in the art.

Another preferred embodiment of the present invention is shown in FIGS. 33–37. In this regard, FIGS. 33 and 34 show rear elevational and side cross-sectional exploded views of a prosthetic knee, generally at 200. The prosthetic knee 200 includes a first fixation means adapted for fixation to one of the bones, which is shown in the form of a femoral component 202. The femoral component 202 is preferably shaped so as to be disposed upon a resected femur.

The femoral component 202 is shown to include a first bearing surface 204 that preferably includes at least two, convex, laterally adjacent, arcuate bearing portions of differing radii. As described here, the first bearing surface 204 represents at least a substantial portion of the inferior surface of the femoral component 202 when considered in a medial-lateral direction. The arcuate bearing portions are shown in this arrangement to each include a pair of condylar portions 206 and 208. The condylar portions 206 and 208 each include two laterally spaced apart condyloid elements defined by laterally spaced, arcuate segments of different radii. As such, each condyloid element within a given condylar portion has a different axis of rotation. Preferably, these condyloid elements are provided as a first inner condyloid element 210, a first outer condyloid element 212, a second inner condyloid element 214 and a second outer condyloid element 216. The inner condyloid elements 210 and 214 are each constructed to a substantially matching radius of curvature and the outer condyloid elements 212 and 216 are each constructed to a substantially matching radius of curvature as well. In the embodiment shown in the accompanying drawings, the radius for the inner condyloid elements is substantially larger than that corresponding to the outer condyloid elements. For example, in one embodiment, the inner condyloid elements 210 and 214 are of radius 1.645 in., while the outer condyloid elements 212 and 216 are of radius 0.800 in. It will be appreciated, however, that any suitable radius selections may be made for these or any other chosen configuration for the condyloid elements making up the condylar portions 206 and 208. In order to enhance a smooth sliding transition of area contact between the inner condyloid elements and the outer condyloid elements, the radii of the inner condyloid elements and the outer condyloid elements preferably intersect. It will be appreciated that any of the arrangements previously described or other arrangements for the first bearing surface 204 may also be suitable.

The prosthetic knee 200 is also shown to include a second fixation means adapted for attachment to the other bone, which is shown in the form of a tibial component 218. The tibial component 218 includes an integral device for enhancing a secured relation of the tibial component 218 to a resected tibia. This is provided in a preferred embodiment as a fixation shaft 220 that is operable for being inserted for fixation into a tibial intermedullary canal. One preferred shape for the fixation shaft 220 is an elongated conical shape that is insertable into a correspondingly shaped tibial intermedullary canal, although other suitable shapes may be used. The tibial component 218 preferably includes means for engaging a bearing element as will be discussed below. This may be provided as a recess 222 that is formed in a conical shape which allows for insertion and relative rotation of a portion of the bearing element discussed below. It will be appreciated, however, that this engagement may also be in a form that allows independent anterior-posterior movement, medial-lateral movement and rotational movement. Alternatively, any other suitable means for engaging a bearing element may be used. The tibial component 218 is also shown to include a second bearing surface 224 lying in a plane generally perpendicular to a longitudinal axis of the tibial component 218, which may be defined by the axis of the recess 222.

The prosthetic knee 200 is also shown to include a bearing element 226 disposed between the femoral component 202 and the tibial component 218. The bearing element 226 includes means for engaging the tibial component 218. The engagement between the bearing element 226 and the tibial component 218 may in one form be a rotatable inserted engagement. Preferably, this is provided as an engagement post 228 of complementary shape to the recess 222. As shown in FIG. 33, the engagement post 228 may be truncated at its lower end. The bearing element 226 also includes a lower bearing surface 230 that is operable for engaging the second bearing surface 224 in a sliding rotatable manner. While the means for engaging the tibial component 218 is provided as set forth above, other suitable means may be used. For example, this engagement may also be in a form that allows limited or unlimited movement in some or all directions within a horizontal plane as a floating bearing situation. As such, the present invention contemplates the possibility of three degrees of freedom between the bearing element 226 and the tibial component 218, namely, anterior-posterior motion, medial-lateral motion and rotation. Simultaneous motion in any or all of these directions is thus contemplated.

The bearing element 226 also includes an upper bearing surface 232 that is a complementary concave surface for engaging the various components forming the first bearing surface 204 of the femoral component 202. In this regard, the upper bearing surface 232 is shown to include a first inner concave surface 234, a first outer concave surface 236, a second inner concave surface 238 and a second outer concave surface 240. These surfaces are preferably shaped in a complementary relation to the first inner condyloid element 210, first outer condyloid element 212, second inner condyloid element 214 and second outer condyloid element 216, respectively. In particular, the first inner concave surface 234 and the second inner concave surface 238 are formed to substantially the same radius of curvature, while the first outer concave surface 236 and the second outer concave surface 240 are formed to substantially the same radius of curvature. The radii corresponding to these portions will also preferably intersect, as before.

The inner condyloid elements 210 and 214 of the femoral component 202 are preferably operable for being in area contact with the inner concave surfaces 234 and 238 of the bearing element 226 from approximately −6° of flexion, through 0° of flexion, or full extension, to approximately 7½° to 8° of flexion. The outer condyloid elements 212 and 216 are operable for being in area contact with the outer concave surfaces 236 and 240 beyond approximately 7½° of flexion. Sliding rotation of the condyloid elements against the concave surfaces results in a transfer of area contact from the inner surfaces to the outer surfaces at approximately 7½° of flexion. This arrangement provides area contact between the condyloid elements and the concave surfaces over the entire range of flexion. Alternatively, the prosthetic knee 200 of the present invention may include additional condyloid elements and concave surfaces that are suitable for sliding rotation engagement. These surfaces may be in area contact over other ranges of flexion, including the situation where one or more pairs of complementary surfaces are in area contact over the entire range of flexion. As such, the present invention is intended to contemplate arrangements where various combinations of complementary regions of area contact are present over the entire range of flexion.

The presence of area contact between surfaces of the femoral component 202 and the bearing element 226 enhances a stabilized condition of the prosthetic knee 200. This occurs by providing additional surface area in the medial-lateral plane over which load may be generally distributed. This is preferably accomplished through the use of arcuate bearing surfaces as viewed in the medial-lateral plane. Area contact between the femoral component 202 and the bearing element 226 also provides enhanced stability by allowing area contact to be maintained between the femoral component 202 and the bearing element 226 on one side of the anterior-posterior centerline in the event of slight liftoff on the opposite side of the centerline. This arrangement is especially preferred over designs having flat bearing surfaces in the medial-lateral plane in order to provide area contact upon liftoff rather than point contact. This arrangement is also preferred over designs having convex bearing surfaces in the medial-lateral plane, but do not accomplish area contact, in order to provide area contact upon liftoff rather than line contact The bearing element 226 further includes a first stabilization member for enhancing a stabilized condition of the prosthetic knee 200 by both controlling articulation and inhibiting disarticulation between the first bearing surface 204 and the bearing element 226. The first stabilization member is operable to be in proximity with at least a portion of the first bearing surface 204 during a substantial range of flexion. The stabilization member is also operable to provide a stop on the bearing element 226 against which a portion of the first bearing surface 204 may rest when the desired limit of articulation at or beyond full extension is reached. The first stabilization member may be configured to be in close proximity to, and/or in area contact with, a portion of the first bearing surface 204 during one or more substantial ranges of flexion. As such, the present invention contemplates arrangements where the first stabilization member is in close proximity throughout the entire range of flexion, is in area contact throughout the entire range of flexion, or is in two or more regions of close proximity and area contact which may alternate or vary during flexion.

The first stabilization member is provided in a preferred embodiment as a posterior stabilization member 242 disposed adjacent to an anterior surface of the bearing element 226. The posterior stabilization member 242 is operable to limit posterior movement of the tibial component 218 throughout the entire range of flexion, including full extension. The posterior stabilization member 242 preferably takes the form of a rounded protuberance disposed in the central region of the bearing element 226, between the first and second inner concave surfaces 234 and 238 at an anterior location. The posterior stabilization member 242 includes lateral edges which may be generally parallel and substantially perpendicular to the lower bearing surface 230, for providing lateral limits on its travel. It will be appreciated, however, that other suitable shapes for the posterior stabilization member 242 may be used.

To provide means for engaging the posterior stabilization member 242 throughout a substantial range of flexion, a cam 244 is located on the first bearing surface 204. The cam 244 is disposed upon a substantial, but incomplete, portion of the first bearing surface 204 at its central region. As such, the first bearing surface 204 is intended to include at least a portion of the cam 244. The cam 244 is shaped and positioned so that the posterior stabilization member 242 may be in close proximity or in area contact during a substantial range of flexion. Preferably, this close proximity range or area contact is accomplished from approximately −6° of flexion (slight hyperextension) to approximately full flexion. More preferably, the posterior stabilization member 242 is in close proximity to the cam 244 from approximately −6° of flexion to approximately 7½° to 8° of flexion, and is in area contact with the cam 244 from approximately 7½° of flexion to full flexion. Alternatively, other ranges of close proximity and area contact may be used. As with the condyloid elements and concave surfaces previously described, an advantage of the area contact between the posterior stabilization member 242 and the cam 244 is the distribution of load over an enlarged surface area.

Because the articulation of the condylar portions 206 and 208 may be transferred between the inner and outer condyloid elements and corresponding concave surfaces during flexion, the cam 244 is preferably shaped to maintain the same close proximity or area contact with the posterior stabilization member 242 during both articulation regions. For this reason, the cam 244 is formed in part with a radius of curvature approximately equal to the radius of the first and second outer condyloid elements 212 and 216. The posterior stabilization member 242 is therefore able to travel either in area contact with or in close proximity to the cam 244 as the first and second outer condyloid elements 212 and 216 articulate against the first and second outer concave surfaces 236 and 240. This region of simultaneous travel preferably occurs during the same range of flexion as the articulation of the first and second outer condyloid elements 212 and 216, namely, beyond approximately 7½° of flexion.

In addition, the cam 244 is formed in part with region of curvature at its anterior end corresponding to the radius for the first and second inner condyloid elements 210 and 214. In this arrangement, the posterior stabilization member 242 travels either in area contact with or in close proximity to the cam 244 as the first and second inner condyloid elements 210 and 214 articulate against the first and second inner concave surfaces 234 and 238. This region of simultaneous travel preferably occurs during the same range of flexion as the articulation of the first and second inner condyloid elements 210 and 214, namely, between approximately −6° of flexion and approximately 7½° of flexion. Thus, the cam 244 is shaped to at least two radii of curvature, one corresponding to articulation of the inner surfaces, and the other to articulation of the outer surfaces.

The cam 244 is preferably formed to have specifically shaped lateral walls that are complementary to the lateral edges of the posterior stabilization member 242. Thus, the insertion of the posterior stabilization member 242 within the cam 244 is operable to limit lateral movement between the femoral component 202 and the bearing element 226.

This enhances a stabilized condition of the prosthetic knee 200 as a whole.

The cam 244 is also preferably operable to inhibit disarticulation at the desired limit of full extension or hyperextension. This is accomplished by allowing the posterior stabilization member 242 to contact the anterior end of cam 244 in an abutting relation. This limiting contact is possible regardless of whether the first stabilization member 242 and the cam 244 are in close proximity or in area contact during predetermined ranges of flexion. When the posterior stabilization member 242 contacts the anterior end of the cam 244, this represents either a limit reached at the end of the desired articulation range, or the engagement of these components after slight disarticulation, in the situation where the posterior stabilization member 242 is maintained in close proximity during flexion.

It will be appreciated that other suitable shapes and ranges of engagement for the posterior stabilization member 242 and the cam 244 may be employed. For example, the posterior stabilization member 242 and the cam 244 may have a single longitudinal region of protrusion and corresponding recess or two or more longitudinally sequential regions of protrusions and corresponding recesses that enhance stability by distributing load additionally over a greater surface area in the medial-lateral plane. The posterior stabilization member 242 and the cam 244 may also have one or more laterally adjacent regions of condyloid elements and concave surfaces incorporated into their surfaces that also enhance stability by additionally distributing load. These surfaces are preferably shaped so that their engagement follows and complements the engagement of the condyloid elements 210, 212, 214 and 216 and the concave surfaces 234, 236, 238 and 240 over one or more of the same ranges of flexion. A single region of protrusion and corresponding recess may complement the engagement of the condyloid elements with the concave surfaces over a portion, up to the entire range, of flexion. Multiple regions of longitudinally sequential protrusions and recesses, or laterally adjacent condyloid elements and concave surfaces, may complement the engagement of the condyloid elements with the concave surfaces partially or completely over two or more regions of flexion, and may complement each other to cause sequential engagements covering up to the entire range of flexion.

Figure 35:
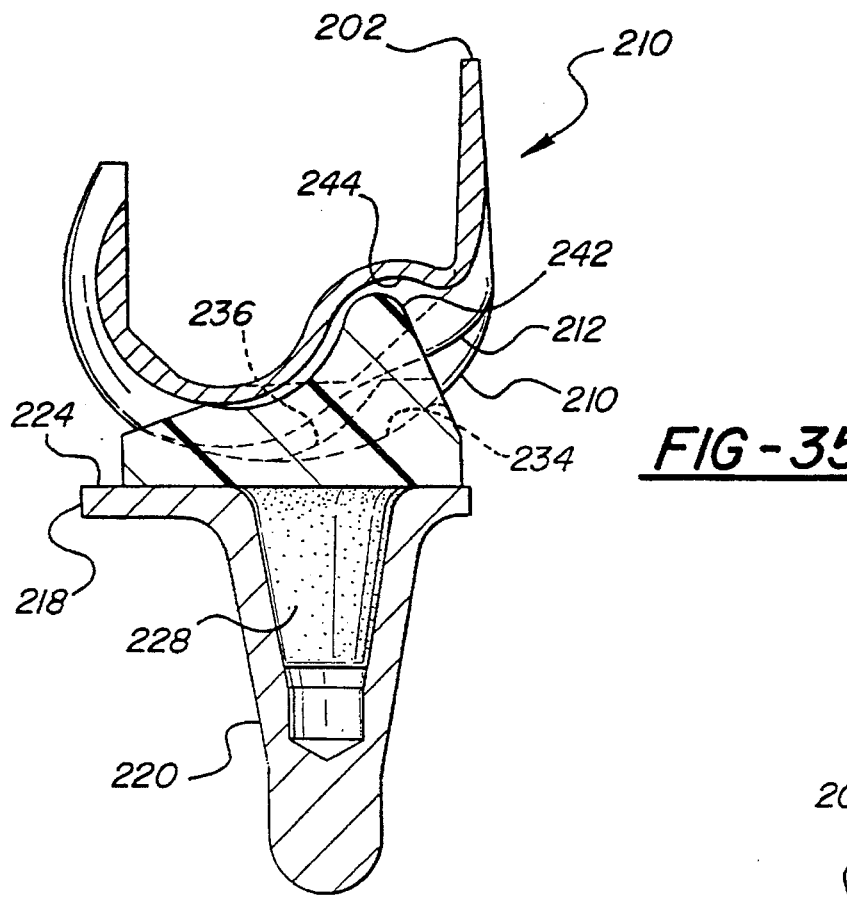
FIG. 35 is a side cross-sectional view of the embodiment of the knee shown in FIG. 33 at 0° flexion.
Figure 36:
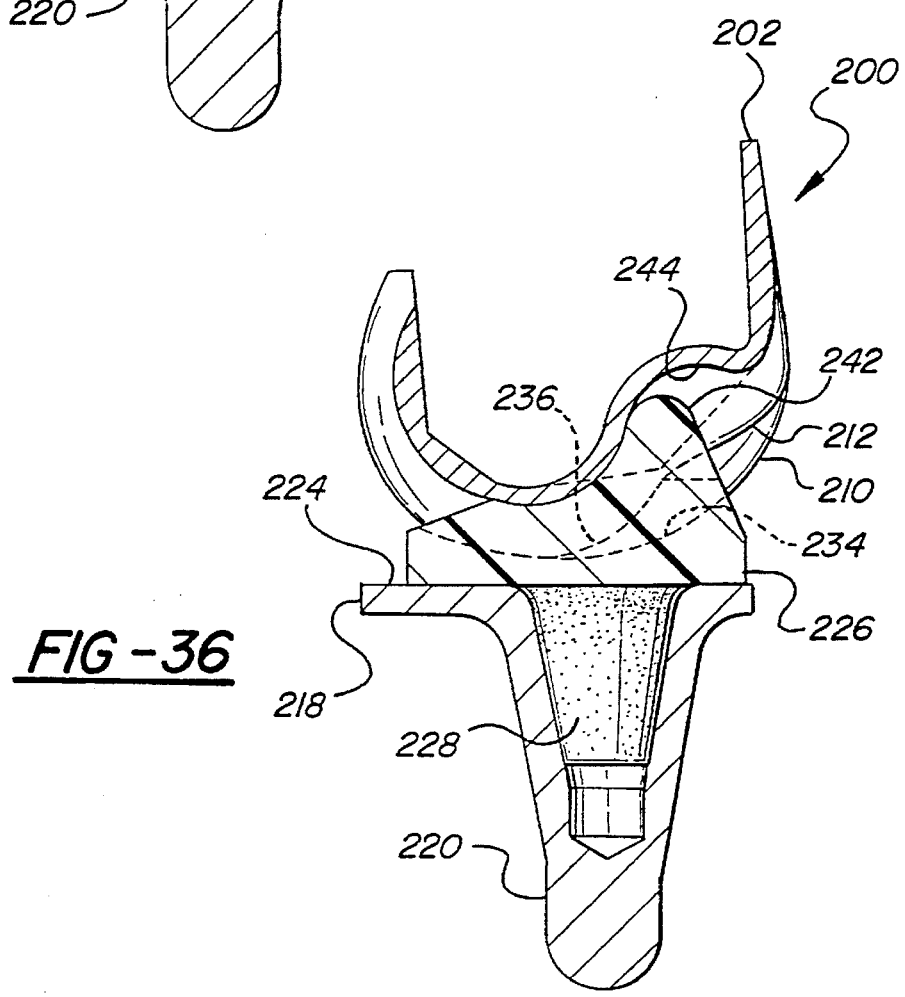
FIG. 36 is a side cross-sectional view of the embodiment of the knee shown in FIG. 33 at 7½° flexion.
Figure 37:
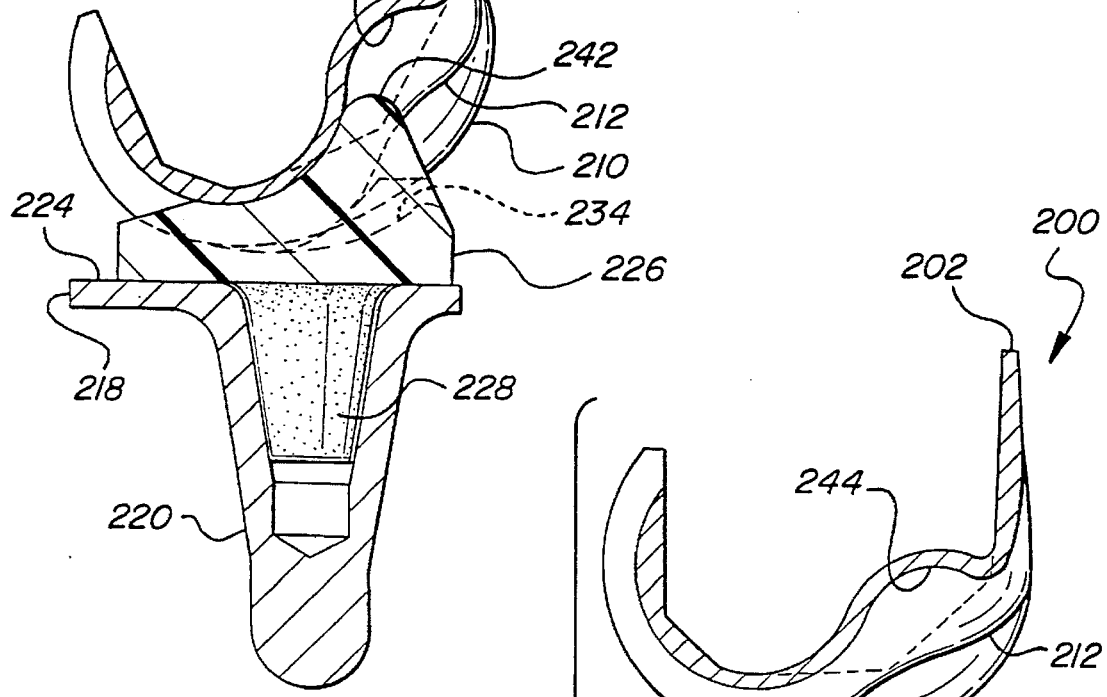
FIG. 37 is a side cross-sectional view of the embodiment of the knee shown in FIG. 33 at intermediate flexion.

Referring now to FIGS. 35–37, there are shown three side cross-sectional views of the same device shown in FIGS. 33 and 34, but in assembled form, and at three stages of articulation. For ease in understanding, similar components have retained similar reference numerals throughout. FIG. 35 is a side cross-sectional view of the prosthetic knee 200 at approximately full extension, or 0° flexion. At this stage, the first inner condyloid element 210 and the second inner condyloid element (not shown) are in area contact with the first inner concave surface 234 and the second inner concave surface (not shown). In this embodiment, the posterior stabilization member 242 is in proximity to, but is not in contact with, the cam 244.

FIG. 36 is a side cross-sectional view of the prosthetic knee 200 at approximately 7½° flexion. At this stage, the first inner condyloid element 210 and the second inner condyloid element (not shown) are in area contact with the first inner concave surface 234 and the second inner concave surface (not shown). The first outer condyloid element 212 and the second outer condyloid element (not shown) are simultaneously in area contact with the first outer concave surface 236 and the second outer concave surface (not shown). This simultaneous area contact occurs at the transition point between the respective arcuate portions. The posterior stabilization member 242 begins its contact with the cam 244.

FIG. 37 is a side cross-sectional view of the prosthetic knee 200 at intermediate flexion. At this stage, the first outer condyloid element 212 and the second outer condyloid element (not shown) are in area contact with the first outer concave surface 236 and the second outer concave surface (not shown). The posterior stabilization member 242 is in area contact with the cam 244.

Figure 38:
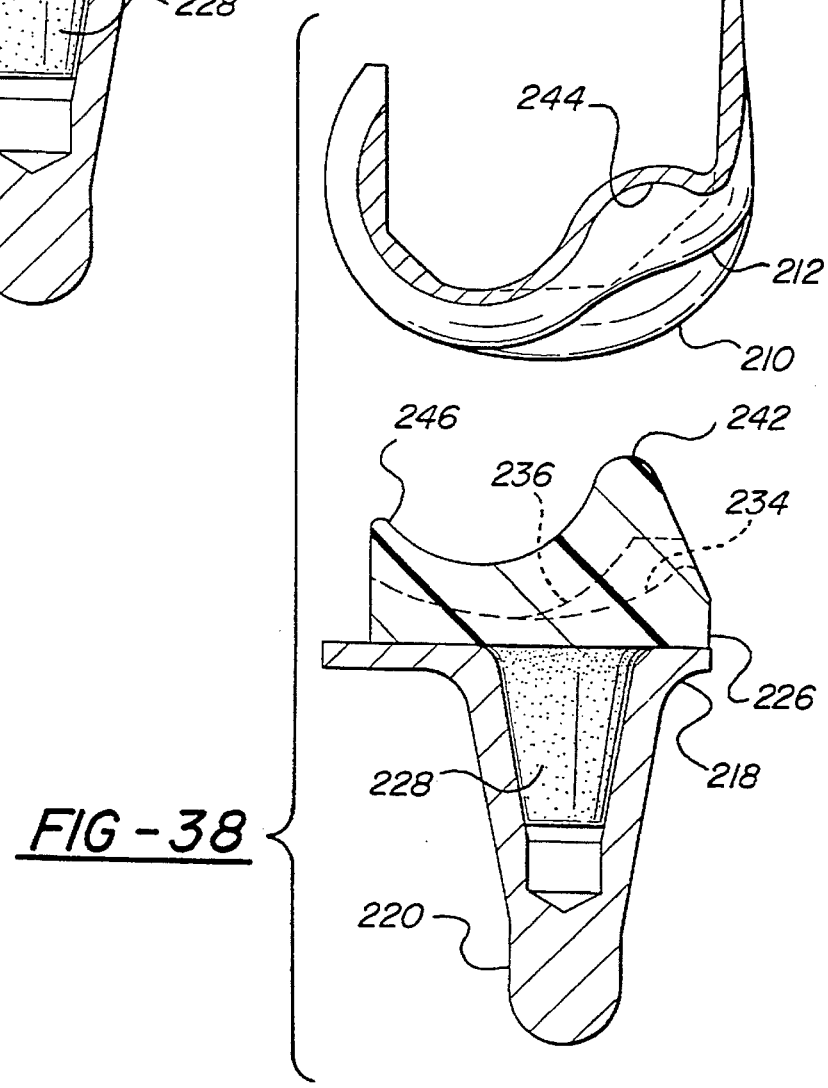
FIG. 38 is an exploded side cross-sectional view of the knee of the present invention including a posterior stabilization member and an anterior stabilization member.

Another embodiment of the present invention will now be discussed with reference to FIG. 38, which shows a prosthetic knee 200 in partial exploded cross-sectional view. In this version, the femoral component 202 and tibial component 218 are substantially the same as previously described. The bearing element 226, however, is shown to further include an anterior stabilization member 246 disposed adjacent a posterior surface of the bearing element 226 which serves to limit anterior movement of the tibial component 218. Most preferably, the anterior stabilization member 246 is also a rounded protuberance disposed in the central region of the first bearing surface 204, between the first and second inner concave surfaces 234 and 238 at a posterior location. The anterior stabilization member 246 is operable to be in close proximity to at least a portion of the first bearing surface 204 over one or more substantial ranges of flexion. In one preferred arrangement, the anterior stabilization member 246 is operable to be in close proximity to the cam 244 over a substantial range of flexion. As with the posterior stabilization member 242, the anterior stabilization member 246 may be similarly constructed to have one or more protrusions and/or recesses that communicate with corresponding recesses and/or protrusions upon the cam 244. The anterior stabilization member 246 preferably has specifically shaped lateral edges, which may be parallel and substantially perpendicular to the lower bearing surface 230, to limit lateral movement of the femoral component 202 with respect to the tibial component 218. In such a configuration, the anterior stabilization member 246 is also able to enhance lateral stabilization of the prosthetic knee 200 during flexion. It will be appreciated that other suitable shapes for the anterior stabilization member 246 may be employed. It will be appreciated that although the anterior stabilization member 246 is shown in conjunction with a posterior stabilization member 242, the anterior stabilization member 246 may also be present without the posterior stabilization member 242.

Figure 39:
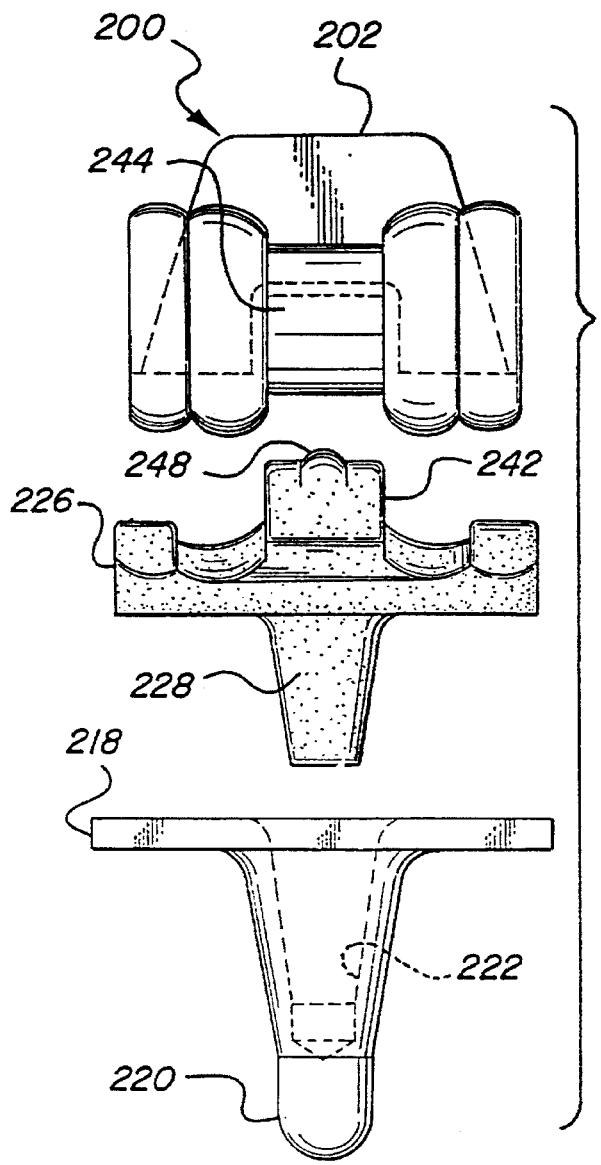
FIG. 39 is an exploded rear elevational view of the knee of the present invention having one version of an additional cooperating surface.
Figure 40:
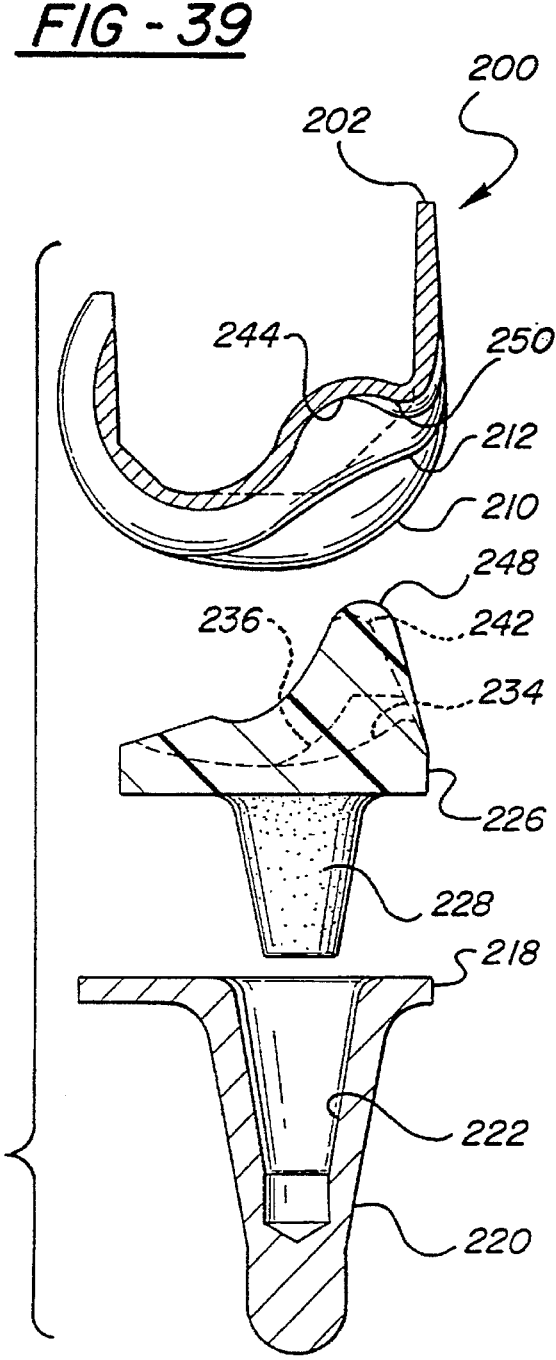
FIG. 40 is an exploded side cross-sectional view of the knee shown in FIG. 39.

Another preferred embodiment of the present invention is shown in FIGS. 39 and 40. In this arrangement, the components are substantially similar to that previously described, except for an additional set of cooperating articulation surfaces for further controlling articulation and enhancing stability and area contact of the prosthetic knee 200. This embodiment is one possible arrangement for additional articulation surfaces on the posterior stabilization member 242 and the cam 244 as previously mentioned. The bearing element 226 includes a first articulation surface 248, preferably located along the arcuate surface of at least a portion of and possibly all of, the posterior stabilization member 242. The first articulation surface 248 is preferably a rounded protuberance having the capability of area contact in several planes at once along its length. FIGS. 39 and 40 show the first articulation surface 248 to be disposed upon the anterior surface and upon a portion of the posterior surface of the posterior stabilization member 242. This configuration allows the first articulation surface to be operable for area contact from approximately −6° of flexion to approximately 7½° of flexion. Other shapes for the first articulation surface 248 may also be employed. Such other shapes may cause the first articulation surface 248 to be operable for area contact over a wider range of flexion. It will be appreciated that any of the additional articulation surfaces set forth herein may be disposed upon the anterior stabilization member 246 alone, or in conjunction with additional lengths of the same or different articulation surfaces disposed upon the posterior stabilization member 242.

The prosthetic knee 200 may also include a corresponding recess upon the femoral component 202 for engaging the first articulation surface 248. This is provided as a cam bearing surface 250 disposed along at least a portion of the length of the cam 244. The cam bearing surface 250 is shaped complementary to the first articulation surface 248 so that the first articulation surface 248 may travel by sliding through the cam bearing surface 250 during the articulation of the remaining components. Preferably, the cooperation of the first articulation surface 248 with the cam bearing surface 250 occurs from approximately −6° of flexion to approximately 7½° of flexion, as set forth in FIGS. 39 and 40, although it may alternatively occur for one or more different portions of the flexion range, including throughout the entire range of flexion. It will be appreciated that the presence of these additional components may result in the variance in dimensions of the femoral component 202 and the bearing element 226.

Figure 41:
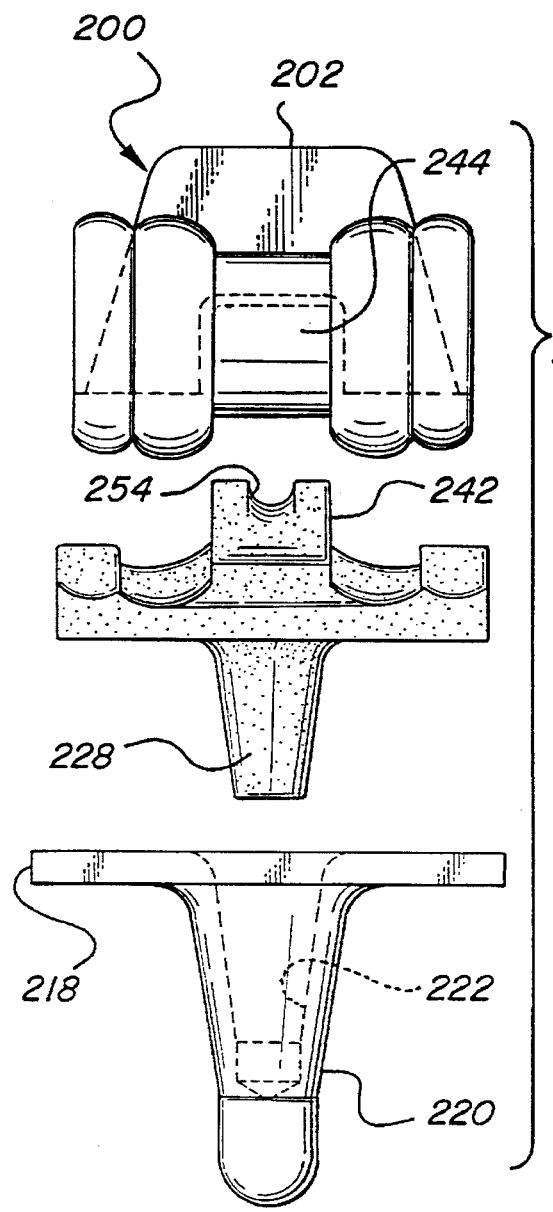
FIG. 41 is an exploded rear cross-sectional view of the knee of the present invention having an alternate version of an additional cooperating surface.
Figure 42:
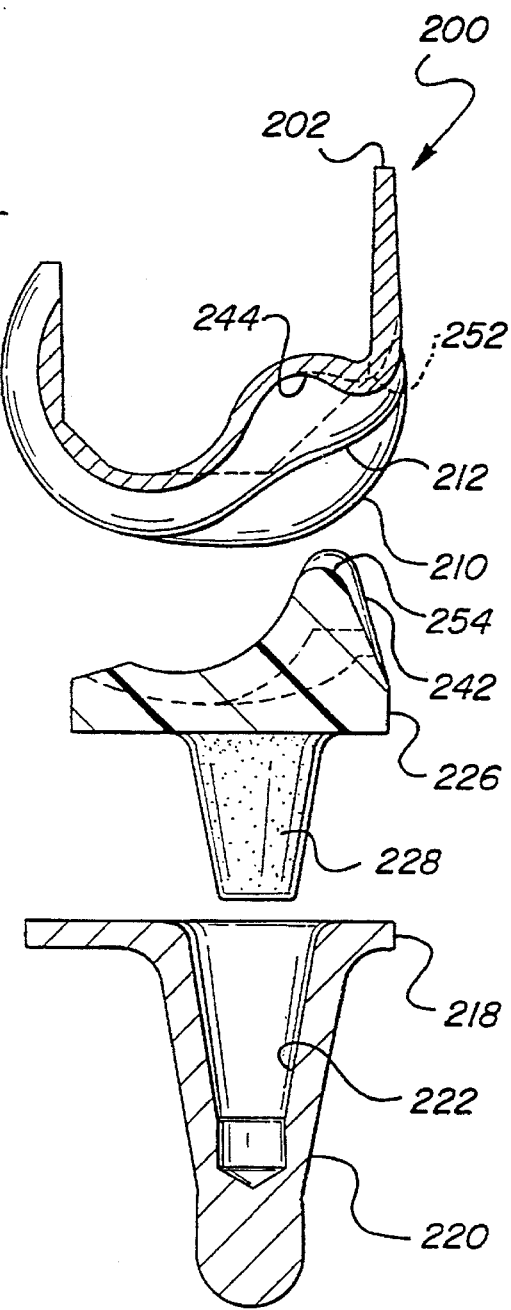
FIG. 42 is an exploded side cross-sectional view of the knee shown in FIG. 41.

Alternatively, as shown in FIGS. 41 and 42, a reverse arrangement may be provided, wherein a second articulation surface 252 is located upon the femoral component 202 for engaging a corresponding recess such as a stabilization member bearing surface 254 upon the bearing element 226. As before, the shape for the second articulation surface 252 may be a rounded shape, although other shapes may be employed. In this arrangement, the second articulation surface 252 is disposed upon the anterior region of the cam 244, with the corresponding stabilization member bearing surface 254 being disposed upon the anterior region and a portion of the posterior region of the posterior stabilization member 242. The preferred range of flexion over which these surfaces are in area contact is from approximately −6° of flexion to approximately 7½° of flexion, as shown in FIGS. 41 and 42, although it may alternatively occur for only one or more portions of the flexion range, including throughout the entire range of flexion. As before, these surfaces may also be disposed in different locations of close proximity along the anterior stabilization member 246 alone, or in conjunction with additional lengths of the same or different cooperating surfaces disposed upon the posterior stabilization member 242.

Figure 43:
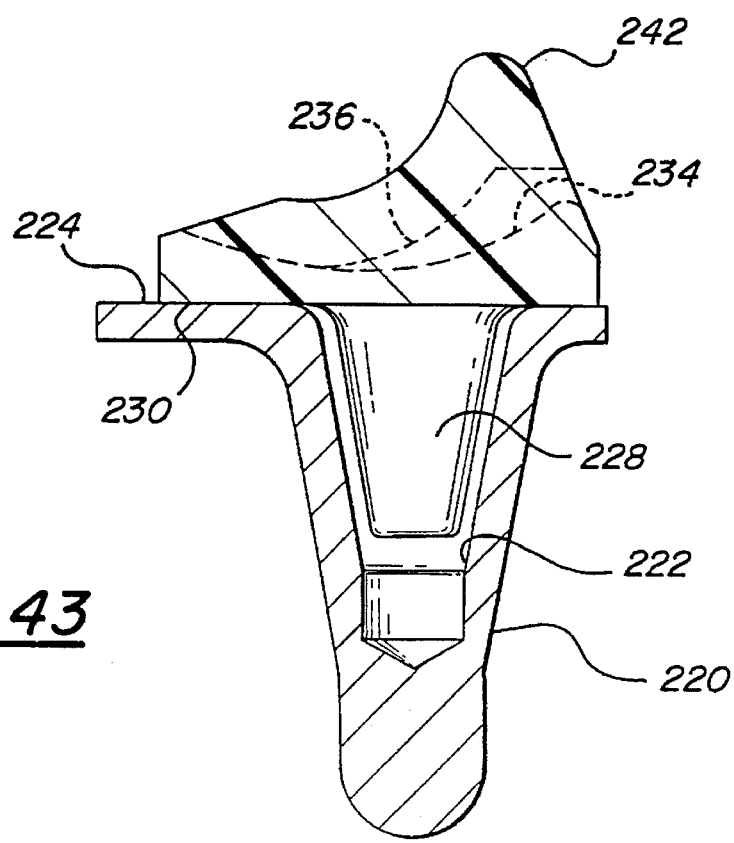
FIG. 43 is a side cross-sectional view of two portions of the knee of the present invention having an alternate version of engagement between the bearing element and tibial prosthesis.

In another embodiment of the present invention, it is contemplated to have three degrees of freedom between the bearing element 226 and the tibial component 218, as previously mentioned. FIG. 43 sets forth such an embodiment, wherein an engagement post 228 of reduced cross-section, compared to the cross-section of the recess 222, is provided upon the bearing element 226. This configuration provides a limited freedom of movement to the bearing element 226 with respect to the tibial component 218. This movement may be in an anterior-posterior direction, in a medial-lateral direction, in rotation and in any combination of the above. A limited floating bearing situation is thus provided. Alternatively, a limited floating bearing situation may also be provided by altering the configuration of the aperture 32, the shoulder bolt 42, the retainer 44 and the spacer 46 in FIGS. 2, 5 and 6. For example, widening the aperture 32 and increasing the head diameter of the shoulder bolt 42 may allow limited movement beyond the anterior-posterior direction alone.

Figure 44:
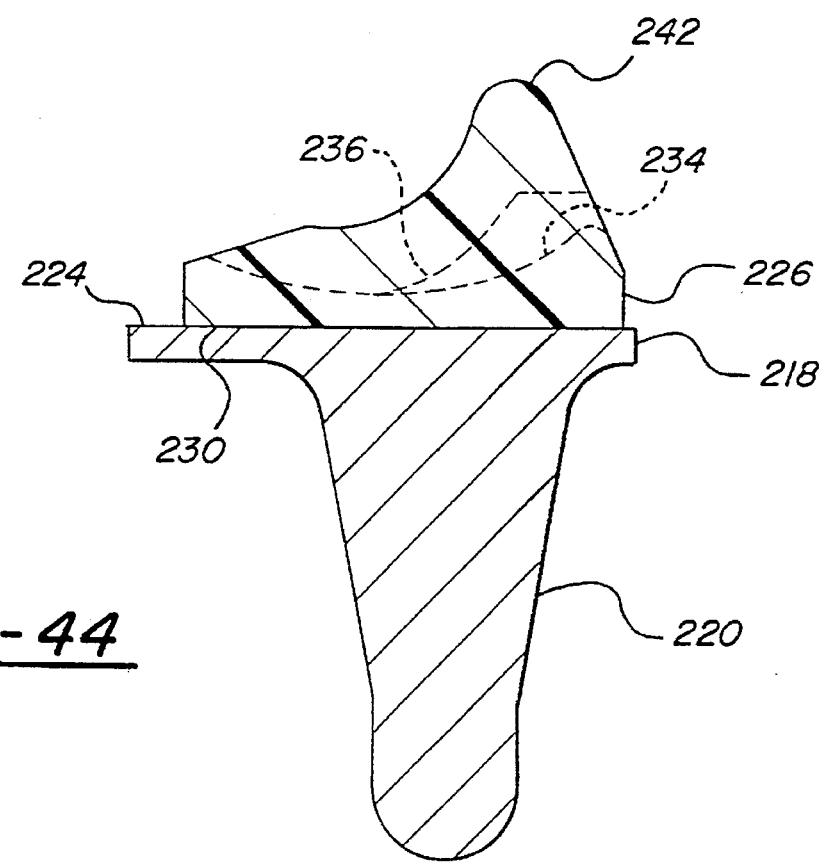
FIG. 44 is a side cross-sectional view of two portions of the knee of the present invention without direct engagement between the bearing element and tibial prosthesis.

FIG. 44 shows an extension of the freedom of movement principle. The bearing element 226 is shown to include a lower bearing surface 230 that is operable to be substantially flush with the second bearing surface 224. In this arrangement, the recess 222 and the engagement post 228 are not included. This provides a floating bearing situation.

In the method of the present invention, a prosthetic knee configured as described above is provided for controlling articulation of an implantable prosthetic device performing a joint between a pair of human or animal bones. The method comprises providing a prosthetic knee including a first bearing surface including at least two arcuate bearing portions of differing radii; a second bearing surface; and a bearing element between the first bearing surface and the second bearing surface and having a complementary concave surface on one side for engaging the first bearing surface and an opposite surface for engaging the second bearing surface in rotatable engagement with the second bearing surface. The bearing element further includes means for inhibiting disarticulation between the bearing element and the first bearing surface, such as a posterior stabilization member. The method further comprises implanting the prosthetic device in a patient; permitting the first bearing surface to slide in area contact upon the bearing element through the arcuate bearing portions of differing radii; permitting the bearing element to rotate with respect to the second fixation means; and permitting the means for inhibiting disarticulation between the bearing element and the first bearing surface to inhibit disarticulation between the bearing element and the first bearing surface.

In the method of the present invention, the means for inhibiting disarticulation between the bearing element and the first bearing surface may comprise a posterior stabilization member, and the step of permitting the means for inhibiting disarticulation to inhibit disarticulation between the bearing element and the first bearing surface comprises permitting the posterior stabilization member to slidably engage a portion of the first bearing surface. The means for inhibiting disarticulation between the bearing element and the first bearing surface may also comprise an anterior stabilization member, wherein the method of the present invention comprises permitting the anterior stabilization member to inhibit disarticulation between the bearing element and the first bearing surface.

It will be appreciated that the principles of the present invention may be applied to any implantable prosthetic device performing a joint between a pair of human or animal bones.

While the above detailed description describes the preferred embodiment of the present invention, it should be understood that the present invention is susceptible to modification, variation and alteration without deviating from the scope and fair meaning of the subjoined claims.

What is claimed is:

1. An implantable prosthetic device forming a knee joint between a femur and a tibia, comprising:
   first fixation means adapted for fixation to the femur;
   a first bearing surface on said first fixation means, said first bearing surface including at least two, convex, laterally adjacent, arcuate bearing portions of differing radii;
   second fixation means adapted for attachment to the tibia;
   a second bearing surface on said second fixation means, said second bearing surface lying in a plane generally perpendicular to a longitudinal axis of said second fixation means; and a bearing element between said first bearing surface and said second bearing surface and having a complementary concave surface on one side for engaging the first bearing surface and an opposite surface for communicating with said second bearing surface so as to allow at least one of relative anterior-posterior movement, medial-lateral movement and rotational movement, said bearing element further including means for inhibiting disarticulation between said bearing element and said first bearing surface.

2. A prosthetic device as claimed in claim 1 wherein said means for inhibiting disarticulation comprises a posterior stabilization member disposed adjacent an anterior surface of said bearing element, said posterior stabilization member operable for inhibiting disarticulation between said first bearing surface and said bearing element.

3. A prosthetic device as claimed in claim 1 wherein said means for inhibiting disarticulation is operable for being in proximity with a portion of said first bearing surface during a substantial range of flexion.

4. A prosthetic device as claimed in claim 2 wherein said first bearing surface includes a cam, and wherein said posterior stabilization member is disposed in close proximity to said cam during flexion of greater than approximately 7½°, whereby minor disarticulation between said first bearing surface and said bearing element causes engagement of said posterior stabilization member with said cam.

5. A prosthetic device as claimed in claim 2 wherein said first bearing surface includes a cam, and wherein said posterior stabilization member is in area contact with said cam during a substantial range of flexion.

6. A prosthetic device as claimed in claim 5 wherein said posterior stabilization member is in area contact with said cam during flexion of greater than approximately 7½°.

7. A prosthetic device as claimed in claim 1 wherein said means for inhibiting disarticulation comprises an anterior stabilization member disposed adjacent a posterior surface of said bearing element, said anterior stabilization member operable for inhibiting disarticulation between said first bearing surface and said bearing element.

8. A prosthetic device as claimed in claim 1 wherein said bearing element includes an engagement device, and wherein said second fixation means includes means operable for engagement with said engagement device.

9. A prosthetic device as claimed in claim 1 wherein said second fixation means includes a recess, and wherein said bearing element includes a post operable for inserted rotatable engagement within said recess.

10. A prosthetic device as claimed in claim 1 wherein said second fixation means includes a recess, and wherein said bearing element includes a post operable for inserted floating engagement within said recess.

11. A prosthetic device as claimed in claim 1 wherein the first bearing surface has a pair of condylar portions, each condylar portion including two laterally spaced apart condyloid elements defined by laterally spaced, arcuate segments of different radii.

12. A prosthetic device as claimed in claim 11 wherein each condyloid element within a condylar portion has a different axis of rotation.

13. A prosthetic device as claimed in claim 11 wherein each condylar portion includes an inner condyloid element and an outer condyloid element, each inner condyloid element operable for being in area contact with a concave surface of said bearing element during a substantial range of flexion, and each outer condyloid element operable for being in area contact with a concave surface of said bearing element during a substantial range of flexion.

14. A prosthetic device as claimed in claim 11 wherein each condylar portion includes an inner condyloid element and an outer condyloid element, each inner condyloid element operable for being in area contact with a concave surface of said bearing element from approximately −6° of flexion to approximately 7½° of flexion, and each outer condyloid element operable for being in area contact with a concave surface of said bearing element beyond approximately 7½° of flexion.

15. A prosthetic device as claimed in claim 13 wherein the area contact between said bearing element and each inner condyloid element represents a first region of sliding contact and the area contact between said bearing element and each outer condyloid element represents a second region of sliding contact, and wherein said first region of sliding contact intersects said second region of sliding contact at approximately 7½° of flexion.

16. A prosthetic device as claimed in claim 1 wherein said means for inhibiting disarticulation includes a longitudinally protruding surface operable for engaging a corresponding longitudinal recess disposed upon said first bearing surface.

17. A prosthetic device as claimed in claim 16 wherein the longitudinal recess is disposed within a cam upon said first bearing surface.

18. A prosthetic device as claimed in claim 16 wherein the longitudinally protruding surface is in sliding area contact with said longitudinal recess from approximately −6° of flexion to approximately 7½° of flexion.

19. A prosthetic device as claimed in claim 1 wherein the first bearing surface includes a longitudinally protruding surface operable for engaging a corresponding longitudinal recess disposed upon said means for inhibiting disarticulation.

20. A prosthetic device as claimed in claim 19 wherein the longitudinally protruding articulation surface is disposed within a cam upon said first bearing surface.

21. A prosthetic device as claimed in claim 20 wherein the longitudinally protruding articulation surface is in sliding area contact with said longitudinal recess from approximately −6° of flexion to approximately 7½° of flexion.

22. A prosthetic device as claimed in claim 1 wherein the means for inhibiting disarticulation includes at least one concave surface operable for sliding area contact with at least one condyloid element disposed upon said first bearing surface throughout a substantial range of flexion.

23. An implantable prosthetic device performing a joint between a pair of human or animal bones, comprising:

a femoral component adapted for fixation to a femur;

a first bearing surface on said femoral component, said first bearing surface including a pair of condylar portions, each condylar portion including an inner condyloid element and an outer condyloid element of differing radii;

a tibial component adapted for fixation to a tibia;

a second bearing surface on said tibial component, said second bearing surface lying in a plane generally perpendicular to a longitudinal axis of said tibial component; and a bearing element between said first bearing surface and said second bearing surface and having a complementary concave surface on one side for engaging the first bearing surface and an opposite surface for communicating with said second bearing surface so as to allow at least one of relative anterior-posterior movement, medial-lateral movement and rotational movement, wherein each inner condyloid element is operable for being in sliding area contact with a concave surface of said bearing element through a substantial range of flexion, and each outer condyloid element is operable for being in area contact with a concave surface of said bearing element through a substantial range of flexion, wherein said bearing element further includes at least one of an anterior stabilization member and a posterior stabilization member operable to inhibit disarticulation between said bearing element and said first bearing surface, and wherein said posterior stabilization member is operable for being in sliding area contact with a cam upon said first bearing surface through a substantial range of flexion.

24. A prosthetic device as claimed in claim 23 wherein at least one of said posterior stabilization member and said anterior stabilization member includes a longitudinally protruding surface operable for engaging a corresponding longitudinal recess disposed upon said first bearing surface.

25. A prosthetic device as claims in claim 23 wherein said first bearing surface further includes a longitudinally protruding surface for engaging a corresponding longitudinal recess disposed upon at least one of said posterior stabilization member and said anterior stabilization member.

* * * * *